（12）United States Patent
Gomersall

(10) Patent No.: US 11,096,666 B2
(45) Date of Patent: Aug. 24, 2021

(54) ULTRASOUND APPARATUS HAVING SWITCHES

(71) Applicant: Knowledge Economy Developments Ltd, Shipley (GB)

(72) Inventor: William Henry Gomersall, Cambridge (GB)

(73) Assignee: Knowledge Economy Developments Ltd, Shipley (GB)

( * ) Notice: Subject to any disclaimer, the term of this patent is extended or adjusted under 35 U.S.C. 154(b) by 519 days.

(21) Appl. No.: 15/951,746

(22) Filed: Apr. 12, 2018

(65) Prior Publication Data

US 2018/0296187 A1    Oct. 18, 2018

(30) Foreign Application Priority Data

Apr. 15, 2017    (GB) .................................. 1706098.9

(51) Int. Cl.
  *A61B 8/00*    (2006.01)
  *G01S 15/89*    (2006.01)
  (Continued)

(52) U.S. Cl.
  CPC .......... *A61B 8/4494* (2013.01); *A61B 8/5207* (2013.01); *A61B 8/54* (2013.01);
  (Continued)

(58) Field of Classification Search
  None
  See application file for complete search history.

(56) References Cited

U.S. PATENT DOCUMENTS 4,127,034 A * 11/1978 Lederman .............. G01N 29/06
                                                        367/7
5,902,241 A *  5/1999 Seyed-Bolorforosh ......................
                                                        G01S 7/52046
                                                        600/443

(Continued)

FOREIGN PATENT DOCUMENTS

GB         2512115 A    9/2014
WO     2014/001962 A1   1/2014

OTHER PUBLICATIONS

Ng et al., "Wavelet restoration of medical pulse-echo ultrasound images in an EM framework". IEEE Transactions on ultrasonics, ferroelectrics, and frequency control, vol. 54, No. Mar. 3, 2007, pp. 550-568. (Year: 2007).*

(Continued)

*Primary Examiner* — Yi-Shan Yang
(74) *Attorney, Agent, or Firm* — Richard M. Goldberg

(57) ABSTRACT

An ultrasound apparatus includes transducers, switches, a pulser, receiver, and processing unit, each transducer connected to the pulser and receiver via one switch and a single communications channel; the processing unit includes a memory and processor, is connected to the pulser and receiver, and identifies a first number that indicates a first aperture size, generates responses from the transducers, and processes the responses to produce image data; and the processor generates each response by selecting contiguous or non-contiguous transducers, the number being equal to the first number, for each switch connected to a selected transducer, sending a signal instructing the switch to connect the transducer to the communications channel, sending instructions to simultaneously fire selected transducers, with a pulse provided simultaneously to each selected transducer via the communications channel, and receiving a single response via the communications channel and receiver, which is the combination of outputs of the selected transducers.

20 Claims, 23 Drawing Sheets

(51) Int. Cl.
 *G01S 7/52* (2006.01)
 *A61B 8/08* (2006.01)
(52) U.S. Cl.
 CPC ........ *G01S 7/5208* (2013.01); *G01S 7/52079* (2013.01); *G01S 15/8915* (2013.01); *A61B 8/461* (2013.01); *A61B 8/56* (2013.01)

(56) References Cited

U.S. PATENT DOCUMENTS

| | | | | |
|---|---|---|---|---|
| 2005/0124880 A1* | 6/2005 | Shinomura | ......... | G01S 15/8925 600/437 |
| 2015/0086098 A1* | 3/2015 | Nair | ................ | G01S 15/8979 382/131 |
| 2015/0241397 A1* | 8/2015 | Savord | .............. | A61B 8/4444 600/459 |
| 2018/0192994 A1* | 7/2018 | Katsube | .............. | A61B 8/461 |

OTHER PUBLICATIONS

Sapia et al., "Ultrasound image deconvolution using adaptive inverse filtering," Proceedings 12th IEEE Symposium on Computer-Based Medical Systems, 1999, pp. 248-253. (Year: 1999).*

* cited by examiner $$\hat{\mathbf{x}} = (H^H \Sigma_n^{-1} H + S^{-2})^{-1} H^H \Sigma_n^{-1} \mathbf{y} \quad \sim 1201$$

$$\mathbf{m}_k = (H^H \Sigma_{n,k}^{-1} H + S_k^{-2})^{-1} H^H \Sigma_{n,k}^{-1} \mathbf{y} \quad \sim 1202$$

$$\mathbf{m}_0 \approx (H^H H + \eta I)^{-1} H^H \mathbf{y} \quad \sim 1203$$

$$(H^H \Sigma_{n,k}^{-1} H + S_k^{-2}) P^{-1} P \mathbf{m}_k = H^H \Sigma_{n,k}^{-1} \mathbf{y} \quad \sim 1204$$

$$P^{-1} = (H^H H + \eta I)^{-1} \quad \sim 1205$$

Fig. 12

$$H^H H = \begin{bmatrix} H_1^H & H_2^H & H_3^H \end{bmatrix} \begin{bmatrix} H_1 \\ H_2 \\ H_3 \end{bmatrix} = \begin{bmatrix} H_1^H H_1 + H_2^H H_2 + H_3^H H_3 \end{bmatrix}^{\underset{\sim}{1337}}$$

$$H^H y = \begin{bmatrix} H_1^H & H_2^H & H_3^H \end{bmatrix} \begin{bmatrix} y_1 \\ y_2 \\ y_3 \end{bmatrix} = \begin{bmatrix} H_1^H y_1 + H_2^H y_2 + H_3^H y_3 \end{bmatrix}^{\underset{\sim}{1338}}$$

$$m_0 = \left( \begin{bmatrix} H_1^H H_1 + H_2^H H_2 + \cdots + H_n^H H_n \end{bmatrix} + \eta I \right)^{-1} \begin{bmatrix} H_1^H y_1 + H_2^H y_2 + \cdots + H_n^H y_n \end{bmatrix}^{\underset{\sim}{1341}}$$

$$m_k = \left( \begin{bmatrix} H_1^H \Sigma_{n,k,1}^{-1} H_1 + H_2^H \Sigma_{n,k,2}^{-1} H_2 + \cdots + H_n^H \Sigma_{n,k,n}^{-1} H_n \end{bmatrix} + S_k^{-2} \right)^{-1} \begin{bmatrix} H_1^H \Sigma_{n,k,1}^{-1} y_1 + H_2^H \Sigma_{n,k,2}^{-1} y_2 + \cdots + H_n^H \Sigma_{n,k,n}^{-1} y_n \end{bmatrix}^{\underset{\sim}{1342}}$$

$$P^{-1} = \left( \begin{bmatrix} H_1^H H_1 + H_2^H H_2 + \cdots + H_n^H H_n \end{bmatrix} + \eta I \right)^{-1 \underset{\sim}{1343}}$$

*Fig. 13b*

ULTRASOUND APPARATUS HAVING SWITCHES

BACKGROUND OF THE INVENTION

The present invention relates to ultrasound apparatus. It is known to use ultrasound to image inside a body or an object. Typically, ultrasound apparatus includes a probe having a number of transducers, each of which is individually addressed and each of which returns a response. Processing the multiple responses thus produced requires a considerable amount of circuitry and processing power. Therefore, to obtain high quality ultrasound images, it is necessary to use equipment that is both bulky and expensive.

BRIEF SUMMARY OF THE INVENTION

According to a first aspect of the present invention ultrasound apparatus comprising a first plurality of transducers, a first plurality of switches, a pulser, a receiver, and a processing unit, wherein each of said transducers is connected to said pulser and to said receiver via one of said switches and via a single communications channel, and said processing unit includes a memory and a processor, and is connected to said pulser and to said receiver. The processing unit is configured to identify a first number that indicates a first aperture size, generate a first plurality of responses from said transducers, and process said responses to produce image data. The processor is configured to generate each said response by selecting said first number of transducers, wherein said transducers may be contiguous or non-contiguous, for each switch connected to a selected transducer, sending a signal instructing said switch to connect said transducer to said communications channel, sending instructions to simultaneously fire said selected transducers, such that a pulse is provided simultaneously to each of said selected transducers via said communications channel, and receiving a single response via said communications channel and said receiver, said response being the combination of the outputs of the selected transducers.

According to a second aspect of the invention, there is provided a method of producing ultrasound image data, comprising the steps of identifying a first number that indicates a first aperture size; generating a first plurality of responses from a first plurality of transducers; processing said responses to produce image data; and outputting said image data. The step of generating each of said responses comprises the steps of selecting a set of said first plurality of transducers, which set may be contiguous or non-contiguous, the number of selected transducers being equal to said first number; manipulating a first plurality of switches, wherein each of said transducers is connected to a pulser and a receiver via a first communications channel and via one of said switches; instructing the pulser to send a single pulse to said transducers via said first communications channel, such that the pulse is received only and simultaneously by said selected transducers; receiving a single response from said selected transducers via said first communications channel and via said receiver; and storing said response.

According to a third aspect of the invention, there is provided a computer-readable medium comprising instructions which, when executed by a computer, cause the computer to carry out the steps of the above method.

BRIEF DESCRIPTION OF THE SEVERAL VIEWS OF THE DRAWINGS

FIG. 6 illustrates the effect of firing a plurality of transducers shown in FIG. 4a;

FIG. 7 shows a model for the effect of the reflection of scatters to the transducer array shown in FIG. 4a;

FIG. 12 shows equations used by the CPU shown in FIG. 3 during post-processing of ultrasound images;

FIGS. 13a and 13b show a model for the processing of data received by scanning using two or more aperture sizes;

DETAILED DESCRIPTION OF THE INVENTION

Figure 1:
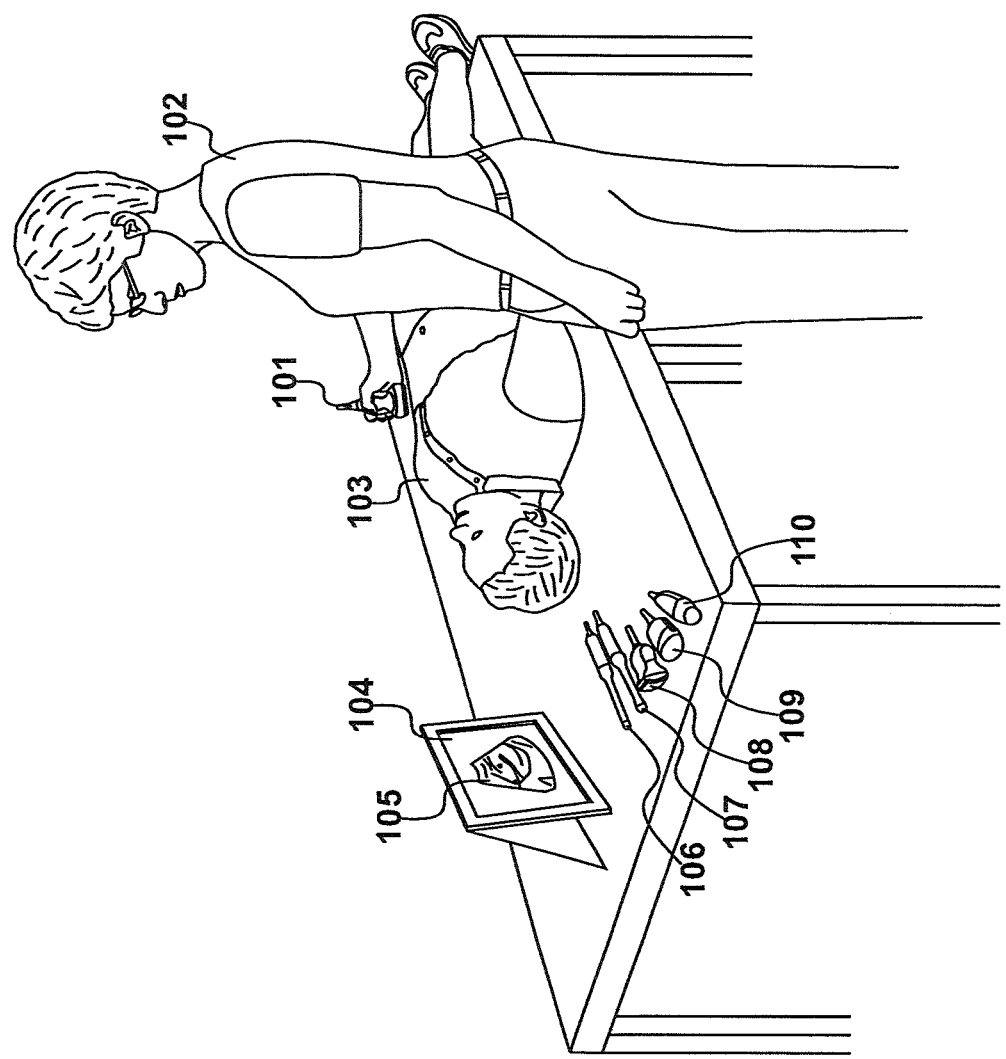
FIG. 1 illustrates an environment in which the invention may be used.

FIG. 1 illustrates an environment in which the invention may be used. An ultrasound probe 101 is being used by a radiographer 102 to image the abdomen of a patient 103. Probe 101 communicates wirelessly with a tablet 104 upon which an image 105 is displayed. Alternative probes 106, 107, 108, 109 and 110 are available for the radiographer's use.

The situation illustrated in FIG. 1 is an emergency, in which patient 103 is being examined outside a hospital setting. Because the radiographer need only carry probe 101 and tablet 104, plus the optional spare probes 106 to 110, the ultrasound apparatus is extremely portable and can be taken into any situation.

However, the apparatus described herein produces images of a high-enough quality to be used in any setting, including the ultrasound department of a hospital or clinic.

Figure 2:
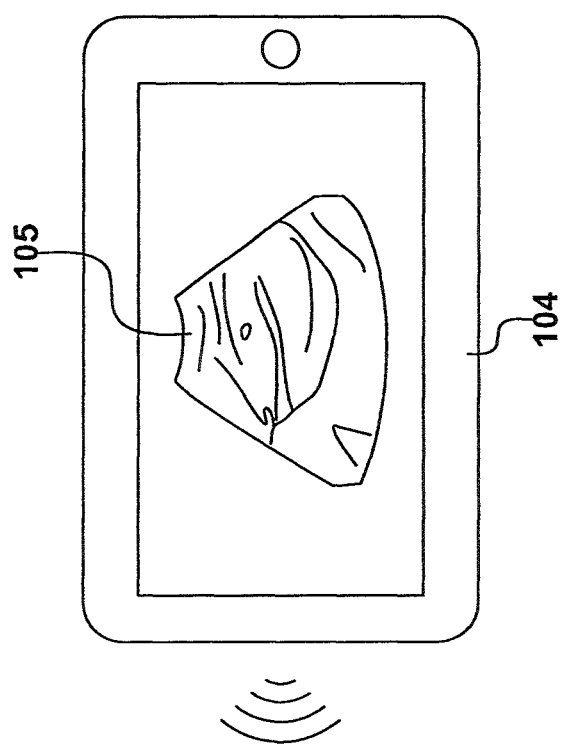
FIG. 2 shows an ultrasound probe and tablet illustrated in FIG. 1.
Figure 2:
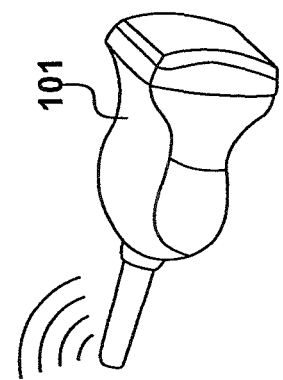

FIG. 2 shows ultrasound probe 101 and tablet 104, upon which an image 105 is being displayed. This is an example of ultrasound apparatus outputting image data to a display device, and in this example the ultrasound apparatus is entirely contained within the casing of probe 101. The apparatus includes a wireless interface that communicates over a radio network with tablet 104. In the example shown here tablet 104 is the display device and is also used to send user settings and instructions to probe 101.

However, other arrangements of the apparatus are envisaged. For example, the display device could be any computing device suitable to receive image data and display it, such as a laptop or desktop computer. Further, it is also possible that a computing device is used only as a display device, with the user settings and instructions being provided by a control device, for example a dedicated device, or an app on a mobile device. In this case, a computer monitor or TV could be used as the display device as computing capability would not be needed.

In a further alternative embodiment, some or all of the ultrasound apparatus might be contained within the display device or a dongle that connects to a display device, rather than inside the ultrasound probe casing.

In any of the above embodiments, the probe may communicate with the display device and/or the control device via a cable rather than a wireless connection.

Figure 3:
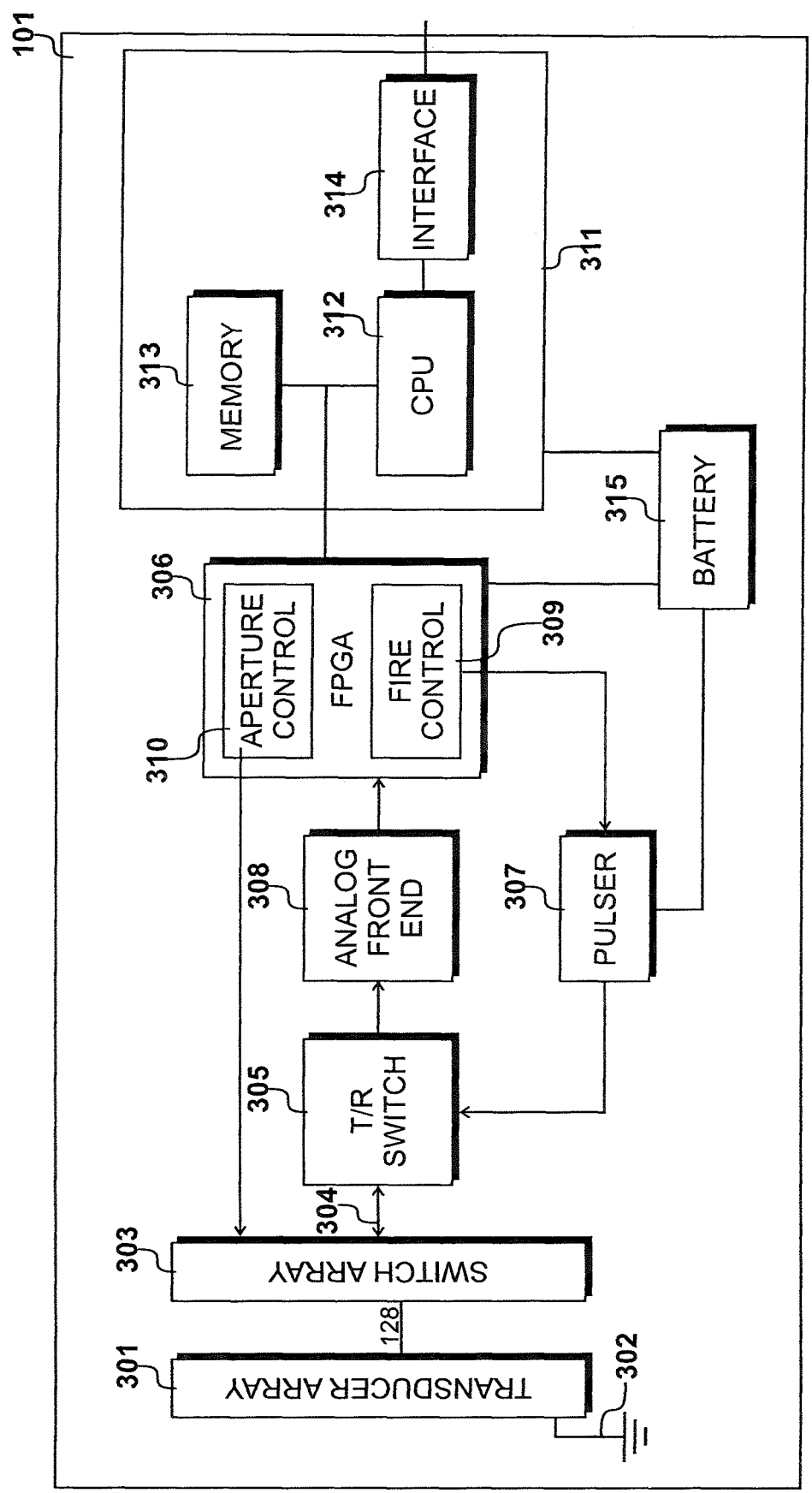
FIG. 3 is a representation of the probe shown in FIG. 1.

FIG. 3 is a diagrammatic representation of probe 101. As described with reference to FIG. 2, in this embodiment all the ultrasound apparatus is contained within the casing of probe 101, and FIG. 3 illustrates this example. However, alternative arrangements are possible.

Probe 101 includes an array 301 of transducers. In this example there are 128 transducers, but this number can vary. More transducers may give a better image, but fewer transducers will reduce the cost. All the transducers are connected to ground as shown at 302. The transducer array 301 is connected to a switch array 303 using 128 channels, as will be described further with reference to FIG. 4, and a single communications channel 304 connects the switch array to a transmit/receive switch 305.

The apparatus includes a fully programmable gate array (FPGA) 306 which is connected to a pulser 307 and a receiver, which in this example is provided by an analog front end 308, both of which are connected to the switch 305.

FPGA 306 includes a fire control process 309 that communicates with pulser 307, and an aperture control process 310 which controls the state of the switches in switch array 303.

The ultrasound apparatus further includes a processing unit 311 which in this example includes a CPU 312, a memory 313 and an interface 314, which in this example is a wireless interface. The elements of the processing unit may be separate or may be provided on a single chip.

A battery 315 provides power to FPGA 306, pulser 307 and processing unit 311.

In a typical prior art ultrasound probe, each transducer is connected by a communications channel to a multiplexer, which maps a number of received responses onto a set of channels to a transmit/receive switch. A typical probe may have an output of 32 channels, meaning that a maximum of 32 transducers can be fired at any one time. To process these 32 channels, 32 analog front ends, 32 pulsers, and a large transmit/receive switch matrix are required. This amount of circuitry means that ultrasound apparatus is expensive, draws a lot of power, and may generate a lot of heat. Further, the apparatus is limited to the number of channels mapped by the multiplexer. To increase the number of channels would require a corresponding increase in circuitry, increasing the aforesaid expense, power requirements and heat.

By contrast, the apparatus shown in FIG. 3 has a single communications channel 304 leading into a single transmit/receive switch 305. It also has a single analog front end and a single pulser. This makes the apparatus considerably less expensive, and reduces its power requirements so that it can be run by a battery 315, thus making the apparatus portable.

In operation, the process performed by ultrasound apparatus 101 is controlled by CPU 312. It provides instructions to FPGA 306 to perform a "sweep" of transducer array 301 using certain parameters, one of which is aperture size. This is expressed as a number of transducers, for example 4.

Upon receiving these instructions, the FPGA, via its aperture control process 310, opens an aperture in transducer array 301 using switch array 303. This will be described further with reference to FIG. 4. It then sends instructions using its fire control process 309 to pulser 307 to provide a pulsed signal. Transmit/receive switch 305 is set to transmit and the pulse signal is provided via communications channel 304 and switch array 303 to the selected transducers. The transmit/receive switch 305 is then set to receive, and a response is received from the transducers via switch array 303 and communications channel 304. This response is supplied to analog front end 308, which carries out amplification and filtering to provide a modified response to FPGA 306.

FPGA 306 provides the modified response to CPU 312 and proceeds to fire another set of transducers. This process repeats until the CPU 312 instructs FPGA 306 to stop. Meanwhile, CPU 312 carries out post-processing on the received signal and supplies it via interface 314 to a display device, which is in this example is tablet 104.

The above circuitry is an example of the claimed invention. Other versions of the circuitry that control a switch array, send a pulsed signal, and process the response, can be used. For example, it is possible that the CPU and FPGA could be combined.

Figure 4A:
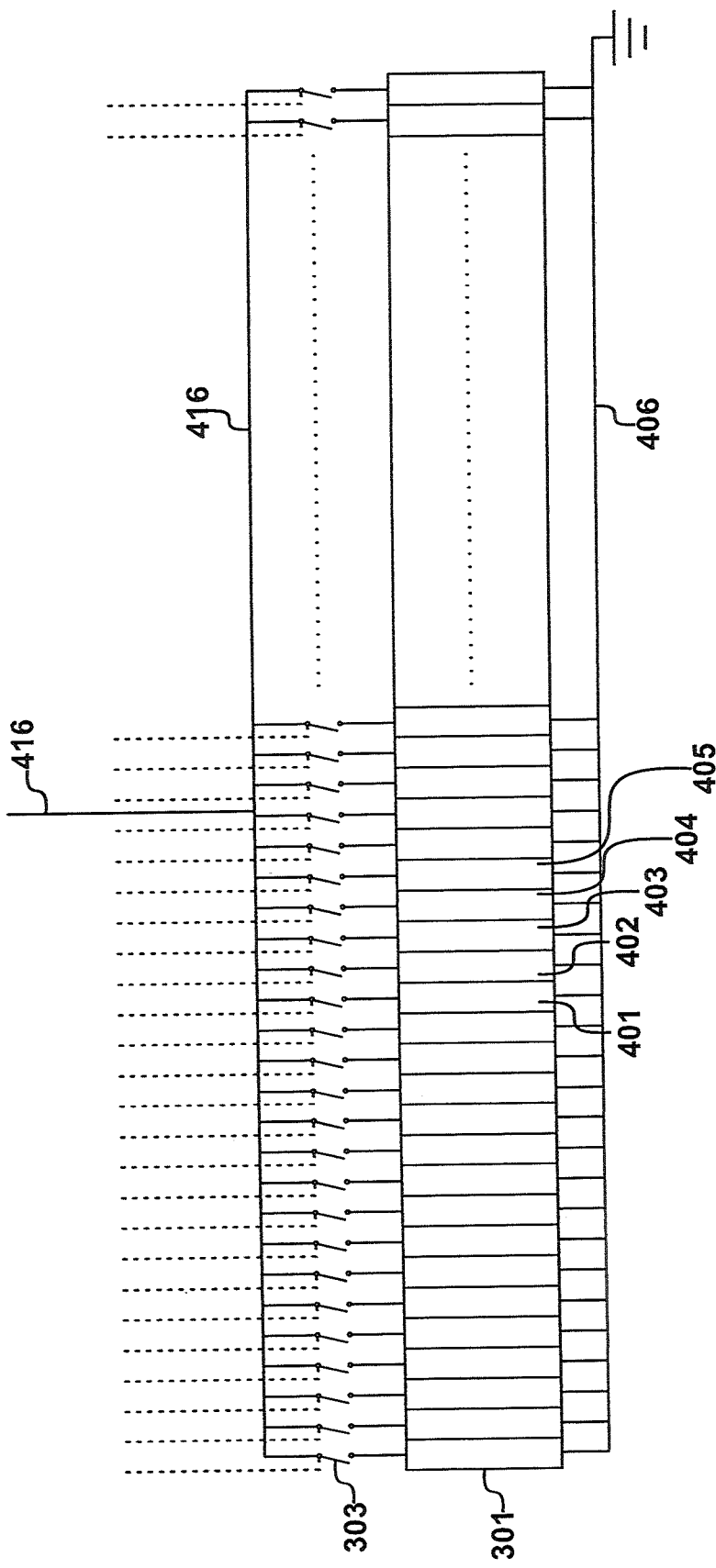
FIGS. 4a, 4b and 4c are illustrations of a switch array and transducer array shown in FIG. 3.
Figure 4B:
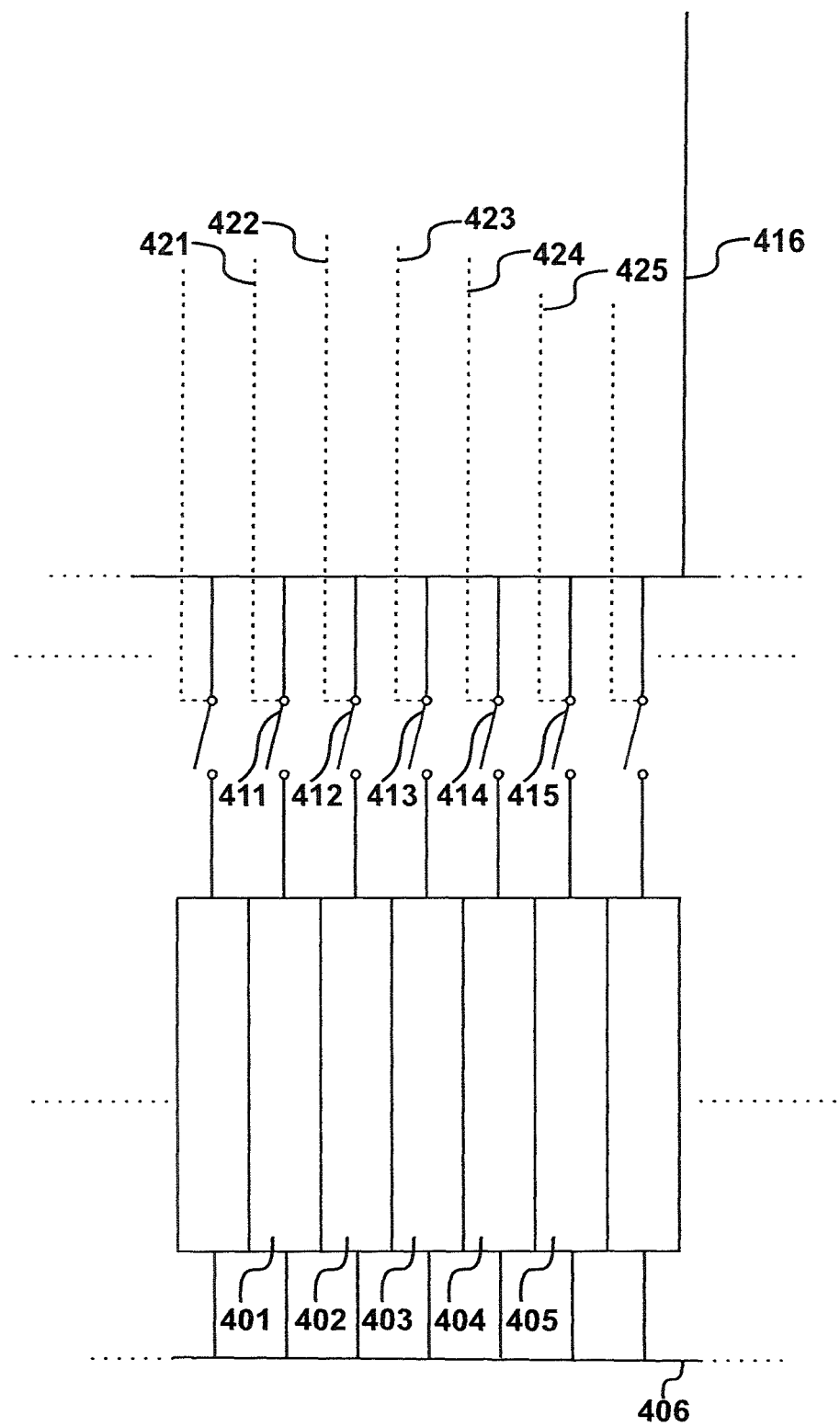

FIGS. 4a and 4b

FIGS. 4a and 4b are diagrammatic illustrations of switch array 303 and transducer array 301. FIG. 4a illustrates the arrays, while FIG. 4b is a close-up of a small number of transducers and switches.

Transducer array 301 is made up of a number of transducers, such as transducers 401, 402, 403, 404 and 405. Each of the transducers is connected to ground by connection 406.

Each transducer is connected to a switch. For example, transducer 401 is connected to switch 411, transducer 402 is connected to switch 412, transducer 403 is connected to switch 413, 404 is connected to switch 414 and 405 is connected to switch 415. Each switch is connected to a single communications channel 416, along which the pulsed signal is sent to the transducers and the response is returned.

In addition, each switch in array 303 has a control channel. For example, switch 411 is connected to control channel 421, switch 412 is connected to control channel 422, switch 413 is connected to control channel 423, switch 414 is connected to control channel 424 and switch 415 is connected to control channel 425. The control channels are connected to aperture control process 310 of FPGA 306, and carry instructions to their respective switches to open and close. No further data is carried along the control channels. In particular, the control channels are not connected to any of the transducers in array 301.

In a typical prior art transducer array, each transducer would have a communications channel back to the circuitry. Each transducer would be fired individually and would provide an individual response. Typically, these responses would be subjected to a delay-and-sum progress in order to produce beamforming. As previously described, the circuitry required to deal with this number of responses limits the maximum possible aperture size of the transducer array. In addition the circuitry can be expensive.

FIG. 4c

Figure 4C:
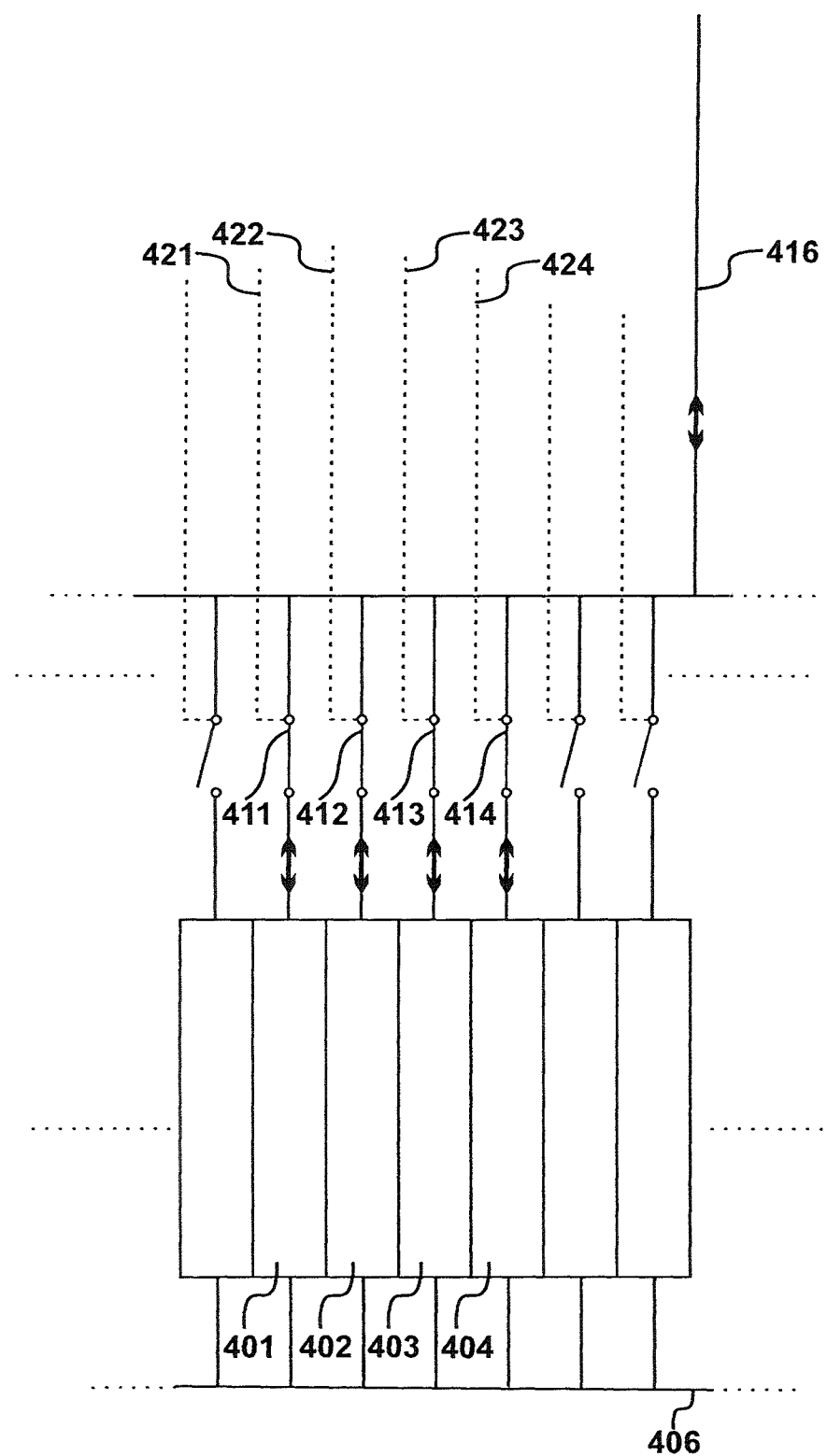

The aperture size in the transducer array shown in FIG. 4 is limited only by the number of transducers. Thus, it is possible to open an aperture of any size from one up to the full array. FIG. 4c shows an example of creating a 4-transducer aperture using the arrays shown in FIGS. 4a and 4c.

To obtain a response using the four transducers 401 to 404, aperture control process 310 sends a signal to switches 411 to 414 via their respective control channels 421 to 424 to close. A pulsed signal is then sent down communication channel 416, as shown by the arrows on the channel. This signal reaches only the transducers with a closed switch, that is, transducers 401 to 404. The arrows on these channels illustrate the pulses and responses. The summed response of these transducers is returned via communication channel 416. To fire the next aperture, aperture control process 310 sends a signal to closed switches to open if necessary, and to further switches to close. For example in order to set the previous aperture along by one transducer, switch 411 receives an open signal via communications channel 421. The state of switches 412 to 414 remains unchanged, and the next transducer along, switch 415, is instructed to close via its communications channel 425. When the pulse is provided via communications channel 416, transducers 402 to 405 are fired.

Thus by opening and closing any combination of switches in array 303, any corresponding combination of transducers in transducer array 301 may be fired. The combination need not be a contiguous set, but could be squared over the whole array. Different aperture sizes and shapes are useful in different ultrasound situations, and the apparatus described herein allows a user to customise the transducer array to produce any required aperture.

Figure 5:
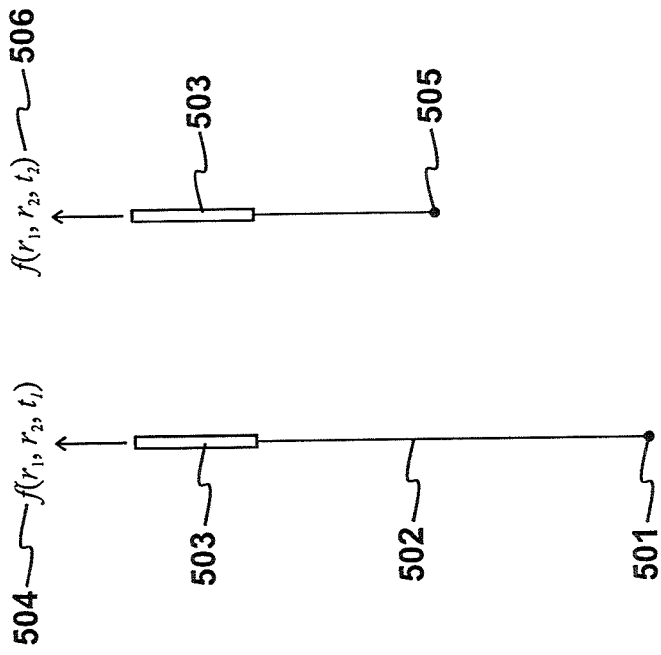
FIG. 5 shows how a pulse is reflected from a point scatterer.

Therefore there is provided ultrasound apparatus comprising a plurality of transducers 301, a plurality of switches 303, a communications channel 416 and a processing unit 311. Each of the transducers is connected to the communications channel by one of the switches. When a set of the transducers is fired, a single response is provided to the processing unit via the communications channel.
FIG. 5

Each transducer in this embodiment is a piezoelectric sensor. It comprises a piezoelectric element of polarised ceramic, with electrodes attached to its opposite faces. It is fired by applying an electric field across the element, causing it to change shape, thus producing a wave that can penetrate some materials and will reflect from others. When this wave hits a reflecting material, known as a scatter, it is reflected back to the transducer. The wave causes the element to change shape again, which produces an electrical response. This response represents the direction of the wave relative to the transducer; in addition, the time taken between the firing of the transducer and the reception of the reflection is known. Thus the response from a transducer can be converted to a time trace by the analog front end. This time trace, optionally filtered and amplified, is used to provide an image of the scatterer.

In other embodiments, different types of ultrasound transducers may be used.

Figure 6:
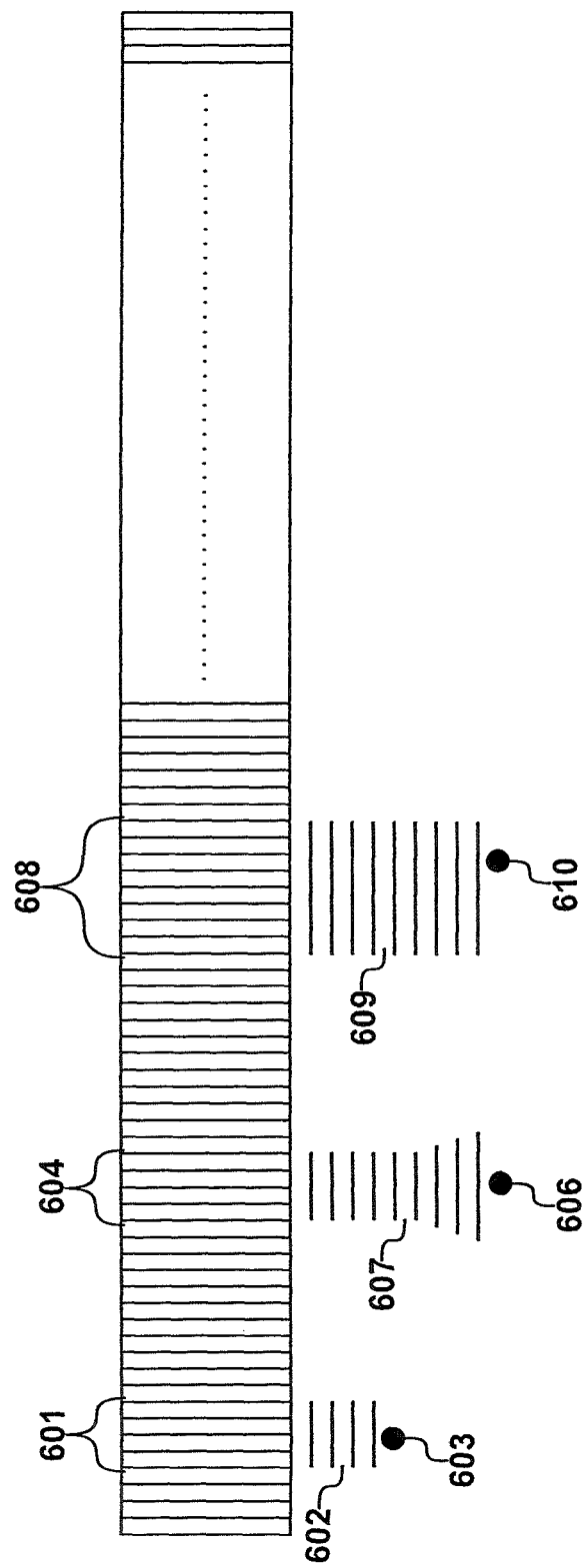

FIG. 5 is a representation of how the reflection from a point scatterer to a transducer is represented by a time trace. The point 501 reflects an ultrasound pulse 502 generated by transducer 503. This results in a time trace 504 which has co-ordinates $r_1$ and $r_2$ in the lateral and elevational directions respectively, and a first time measurement $t_1$, representing the amount of time it took for the pulse to be reflected. A point 505, on the same line as point 501 but at a smaller depth, would have the same lateral and elevational entries in its time trace 506, but a smaller time measurement $t_2$. In theory, it is therefore a simple matter to equate time with depth and provide a position in three dimensions for each scatterer. However, a pulse is not a neat line, but a wave having a focal point, and thus each scatterer is reflected back to more than one transducer.
FIG. 6

FIG. 6 illustrates the effect of firing of a number of transducers in array 301. The transducers are fired together, giving an aperture size corresponding to the number of transducers. For example, a set 601 of four transducers is fired together, resulting in a flat waveform 602 that reflects from scatterer 603, which is at a good depth to be imaged by an aperture size of 4.

A flat waveform tends to diverge. Thus, when an aperture size of 4, such as aperture 604, is used to image a deeper scatterer 606, the flat waveform 607 starts to diverge before it hits the scatterer. This gives a less sharp image.

Aperture 608 has a size of 8, and the waveform 609 that it produces has not diverged before it hits scatterer 610, which is at the same depth of scatterer 606.

Thus, it can be seen that a small aperture effectively images shallow scatterers, while a wider aperture effectively images deeper scatterers.

Figure 7:
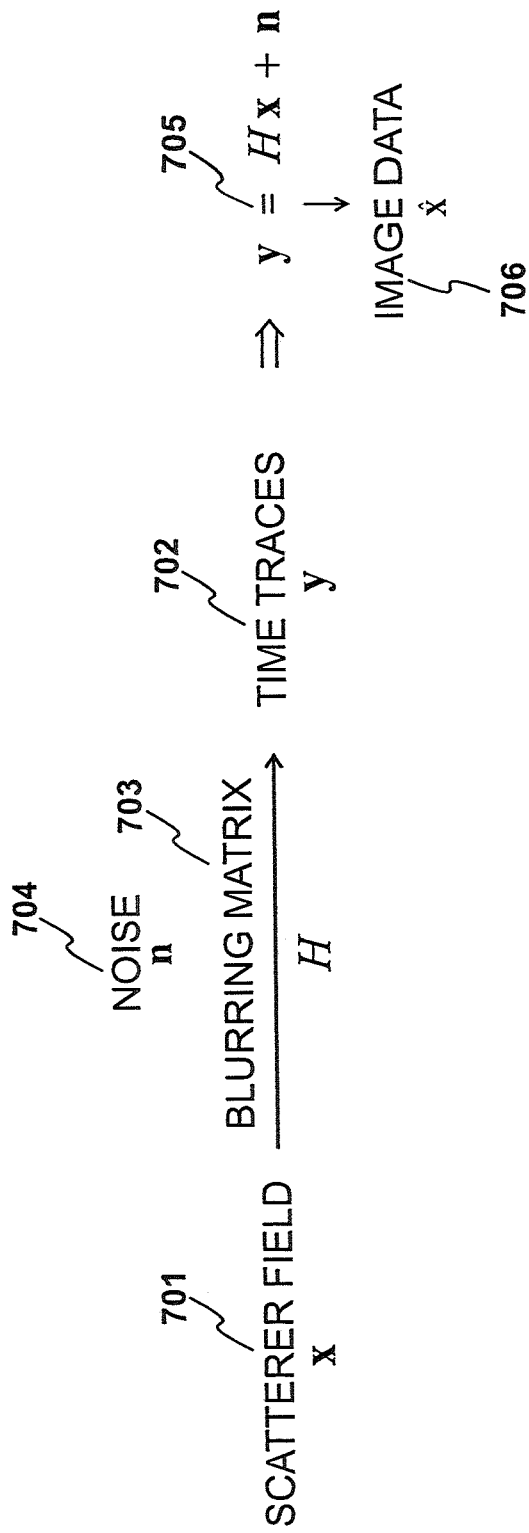

The current consensus in the field of ultrasound is that a flat waveform cannot be used to provide a sharp image, because it does not focus. A typical prior art ultrasound probe will use beamforming, which fires the transducers in an aperture in sequence to produce a focused beam. This provides a focal depth for the probe, and scatterers at this depth are imaged well. However, nearer or further away scatterers are blurry. By contrast, the apparatus described herein creates an aperture by firing transducers together, thus, effectively providing a single, larger, element, that has a flat waveform. Conventionally, it would be assumed that the images produced using this aperture would be too blurry. However, the post-processing method described herein allows the raw time traces to be processed into sharp images using a relatively computationally inexpensive process.
FIG. 7

FIG. 7 shows a model of the effect of the reflection of the scatterers shown in FIGS. 5 and 6 to the transducer array 301. A material to be imaged is considered as a field of scatterers 701. When these are imaged using an ultrasound probe, time traces 702 are produced using the responses from the fired transducers. Thus, for any set of pulses and responses, there is some blurring matrix 703 that transforms the scatterer field 701 into the time traces 702. A noise component 704 is also present. This can be written as equation 705:

$$y=Hx+n$$

The blurring matrix 703 (H) can be discovered by imaging a known scatterer field with an ultrasound probe; the response of that probe is stored and used to calculate the blurring matrix.

Figure 8:
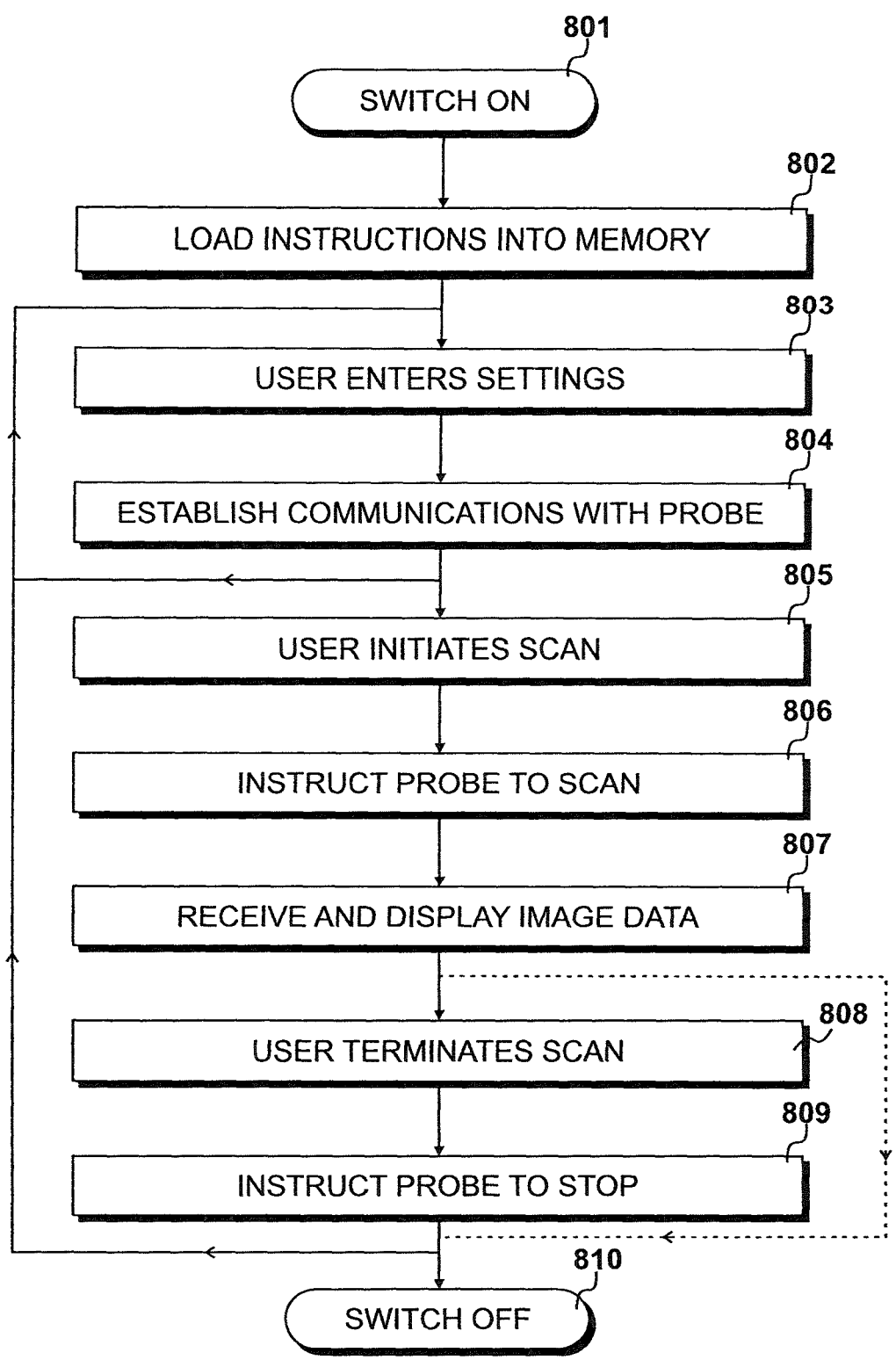
FIG. 8 details steps carried out by the tablet shown in FIG. 1 to receive and display ultrasound images.

Blurring matrix 703 is large and non-sparse, and therefore the original scatterer field 701 in equation 705 cannot be found by simply inverting the blurring matrix. Therefore, a process to arrive at an estimate 706 of the image data is used. The process used in this example will be described further with reference to FIG. 12.
FIG. 8

Figure 9:
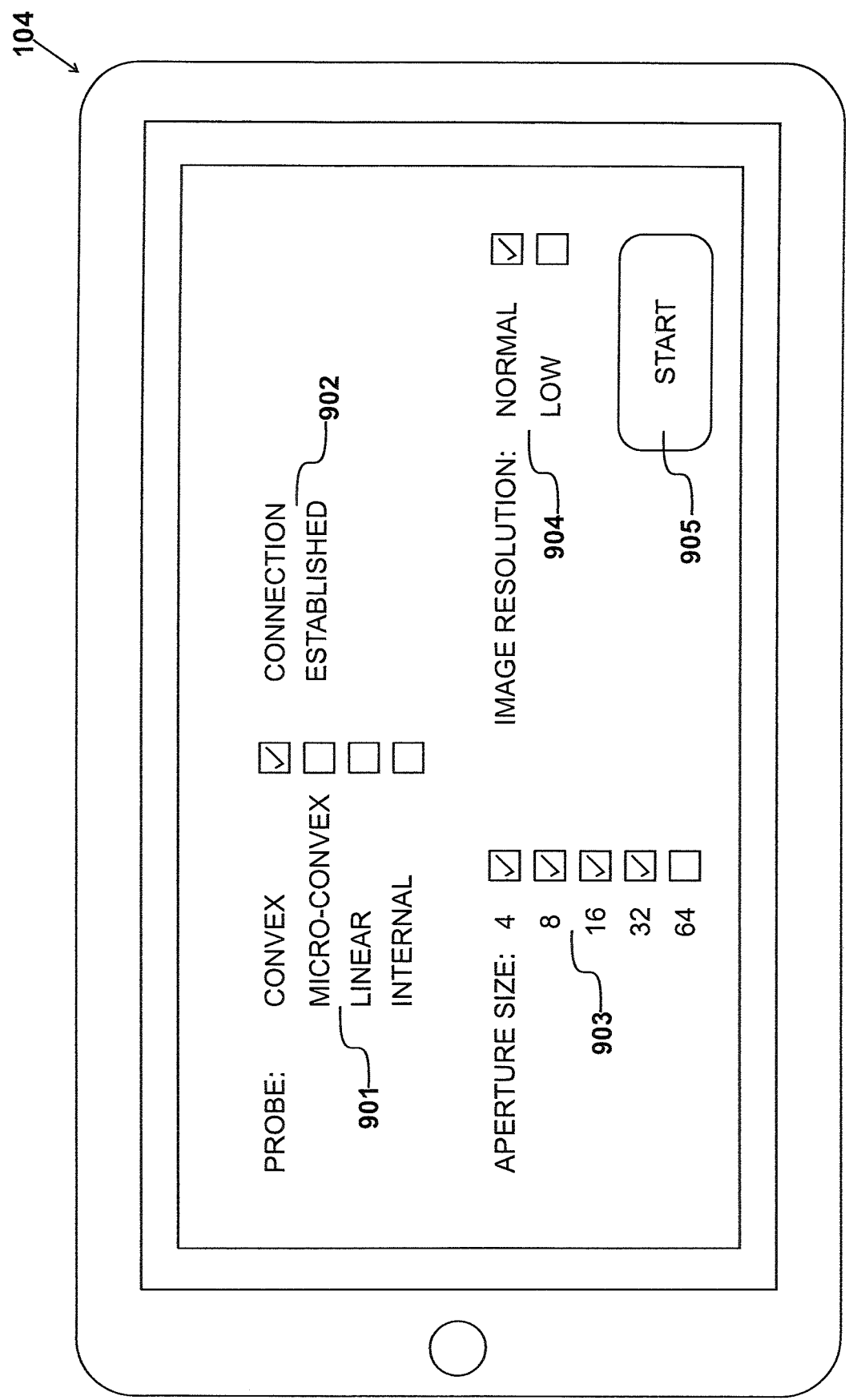
FIG. 9 illustrates a user interface displayed on the tablet shown in FIG. 1.

The process by which ultrasound images are generated and displayed will now be described with reference to FIGS. 8 to 20. FIGS. 8 and 9 show steps taken on tablet 104 to send instructions to probe 101 and display received image data, while FIGS. 10 to 20 detail steps taken by CPU 312 on probe 101 to produce and output the image data.

In other embodiments, these tasks may be separated differently. For example, in an embodiment including a computer and a probe, where the probe contains no processing power, all the processing will take place on the CPU with the computer and there would be no interface between them. Alternatively, the embodiment where the probe is controlled by remote control and the display device merely displays images, the steps described in FIG. 8 would be split between the remote control and the display device. In a further embodiment, the probe could include a small keyboard and screen such that a separate control device is not necessary. Thus, it would be appreciated that the separation of the tasks described herein depends on the type of equipment being used.

In this embodiment, tablet 104 acts as a control device and a display device. Its circuitry is not shown, but in this example includes a CPU, memory, storage, and a wireless network interface. The steps taken by the CPU are detailed in FIG. 8.

At step 801 tablet 104 is switched on and at step 802 instructions are loaded into memory. It is envisaged that the instructions will be implemented as an app that may be downloaded from a networked location, but alternatively the instructions may be preloaded on a dedicated device.

At step 803 a user, such as radiographer 102, enters settings for the scan, as will be described further with reference to FIG. 9. This includes selecting the probe to be used, and therefore at step 804 wireless communication is established with the selected probe, including sending the settings. The user may then change the settings further, including selecting a different probe, and if this occurs communications are re-established and further settings are sent.

When the user is satisfied that the settings are correct, she initiates the scan at step 805, and therefore at step 806 tablet 104 sends instructions to probe 101 to start scanning. At step 807 tablet 104 receives a stream of image data via its wireless interface, and displays it. At step 808 the user terminates the scan, and therefore at step 809 tablet 104 sends instructions to probe 101 to stop scanning. As an alternative to step 808, the connection with the probe may be lost, for example if the wireless link is lost or if the probe's battery runs too low, in which case the scan is terminated without user input.

Once the scan is terminated, the user may return to step 803 to enter new settings and start another scan. Alternatively, tablet 104 is switched off at step 810.

FIG. 9

FIG. 9 illustrates the user interface on tablet 104 that allows the user to enter settings and initiate a scan. Region 901 allows the user to select the probe used, and in region 902 the interface displays whether a connection has been established with the probe.

In region 903 the user may select one or more aperture sizes that are to be used in the scan, while in region 904 the user may specify a low resolution display instead of the standard display, for example if the wireless connection has a low bandwidth.

When all the settings are entered, START button 905 becomes available for the user to press to initiate the scan. At this point the interface shown will be replaced by a stream of, image data, in the corner of which is a STOP button (not shown) for the user to terminate the scan and return to the interface.

FIG. 9 shows an example of a suitable interface for use with the claimed invention. Other envisaged interfaces may include more or fewer settings, such as: more probe settings, features such as recording the scan or broadcasting the scan to another device simultaneously, regions to provide extra information about the patient or the situation, and so on.

FIG. 10

Figure 10:
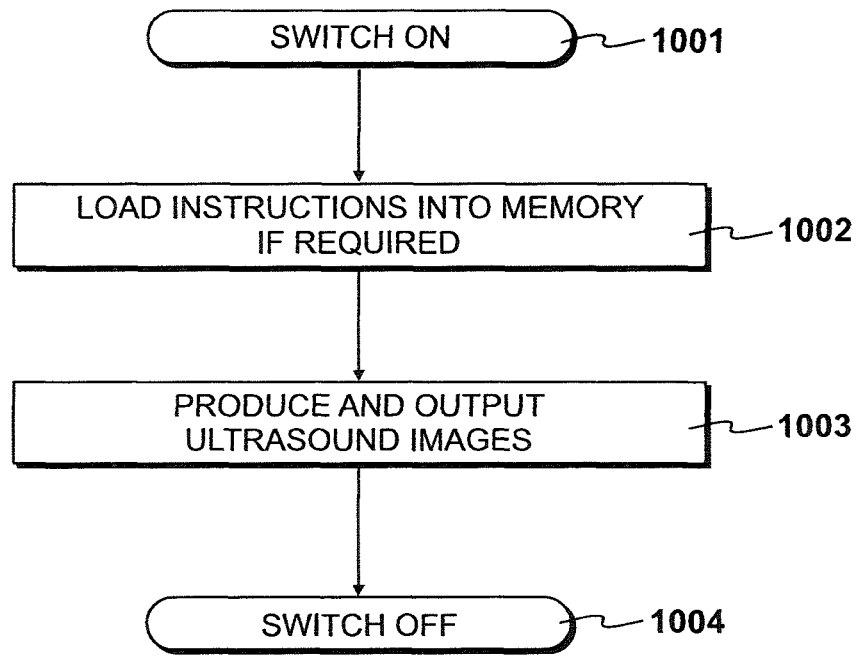
FIG. 10 details steps carried out by the CPU shown in FIG. 3 to carry out an ultrasound scan.

Steps carried out by the CPU 312 on ultrasound probe 101 are described in FIG. 10. At step 1001 the probe is switched on and at step 1002 instructions are loaded if required. Generally these instructions will be stored in memory 313 and do not require loading, but on first use or when an update is required, they may be downloaded from tablet 104, onto which they may have been loaded from a computer-readable medium or via a network. In other embodiments, the location of the stored instructions and the method of downloading new instructions will be dependent upon the nature of the embodiment. For example, if the processing unit is contained within a computer, then the instructions are likely to be loaded from a hard drive and can be installed from a networked location, removable storage device, etc.

At step 1003 ultrasound images are produced and output for display in response to instructions received from tablet 104, and at step 1004 the probe is switched off.

FIG. 11

Figure 11:
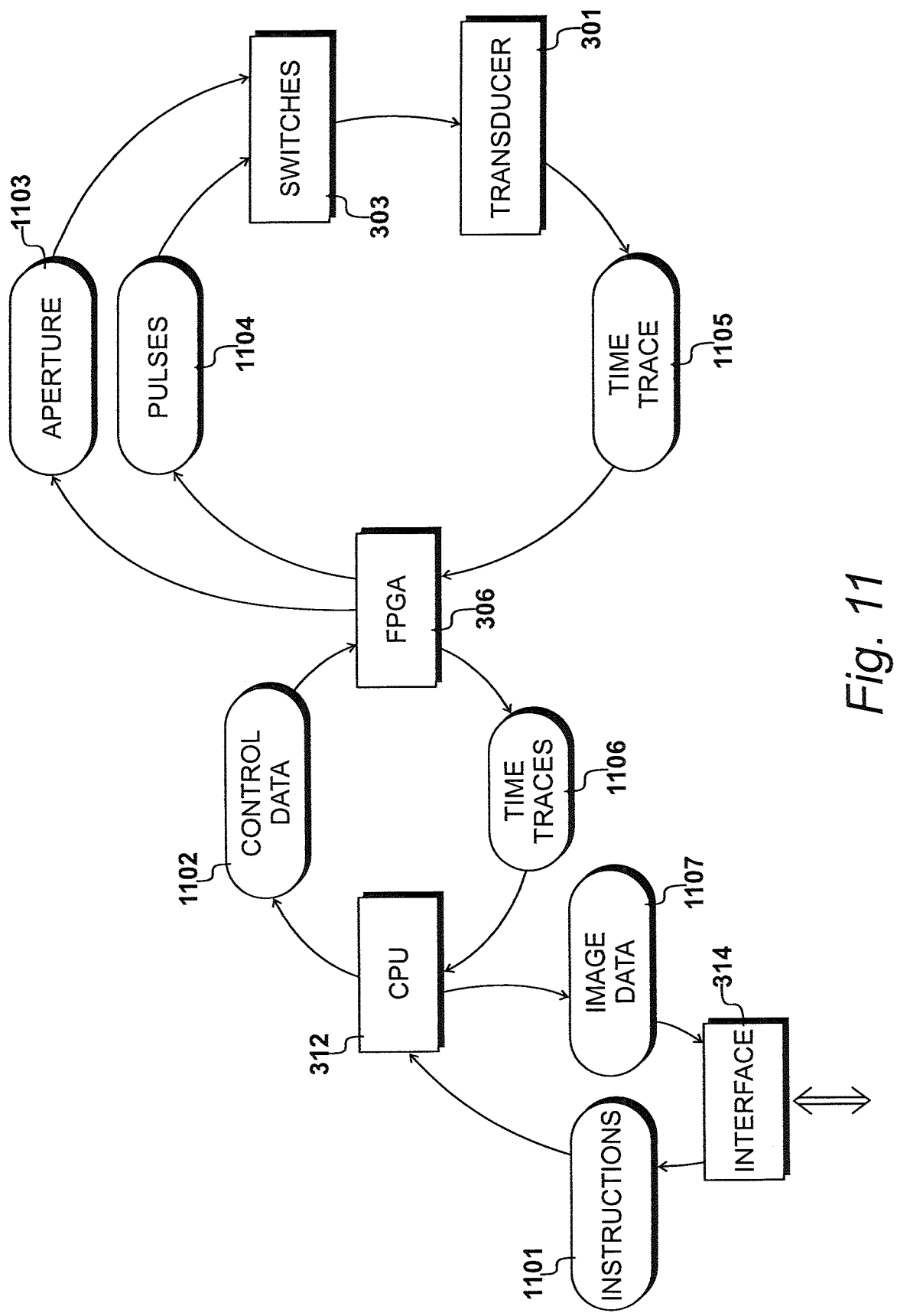
FIG. 11 is an overview of a process step shown in FIG. 10.

FIG. 11 is an overview of the process carried out to produce and output ultrasound images at step 1003. Interface 314 establishes communication with tablet 104, and the ultrasound process is initiated by receipt of settings and instructions 1101 to initiate the scan. On receipt of these, CPU 312 carries out some initial processing and then begins sending control data 1102 to FPGA 306.

Aperture control 310 on FPGA 306 sends instructions 1103 to one or more of the switches in array 303 via the switches' respective control channels, such that a required aperture is created by closing one or more switches. Fire control 309 on FPGA 306 then sends a pulse signal 1104 via the closed switches to transducer array 301, thus firing selected elements.

The response from the selected transducers is converted to a time trace 1105 via analog front end 308 and provided to FPGA 306, which initiates the pulse process again with a new aperture of selected elements. FPGA 306 stores the time traces until a sweep of the transducer array 301 has been completed, and then provides the time traces 1106 for the entire sweep to CPU 312. The CPU then performs post-processing on the time traces 1106 to produce image data 1107, which is output for display via interface 314.

Thus the CPU acts as the overall controller of the process and performs the post-processing on the time traces, while FPGA 306 performs the actual steps of opening an aperture, firing the transducers and routing the time traces back. This is done in response to the control data 1102 produced by CPU 312, which instructs FPGA 306 to perform a sweep of the transducer array 301 using an aperture having particular characteristics. Most typically, the aperture characteristics are its size, ie the number of elements that it contains, and the relative distribution of the elements, ie whether they are contiguous, and if not, how they are to be selected. For example, the aperture may be a contiguous set of 8 elements; or it may be a set of 4 elements, with an element between each selected one, etc. A sweep of this kind starts at one side of the array, opens an aperture of the required size, obtains the time trace, then steps the aperture across by one element and obtains another time trace. This is repeated until the sweep reaches the other end of the array. Further sweep characteristics include, for example, what to do at the edges of the array: whether to stop at the last full aperture of the required size, or to step down in size until the last element is reached.

Other, more complicated sweeps may be performed. For example, control data 1102 may instruct FPGA 306 to fire non-contiguous elements to sweep from the middle outwards, and so on. Any aperture characteristics may be envisaged, as the apparatus allows any number and combination of elements to be fired simultaneously, and the elements may be contiguous or non-contiguous.

When FPGA 306 has completed the sweep instructed in control 1102 it provides the time traces 1106 produced from that sweep back to 312. It then clears its memory and proceeds with the next sweep, as instructed by further control data. This sweep may use the same aperture characteristics as the previous sweep or new characteristics. Thus the apparatus may provide, as with traditional ultrasound probes, a number of sweeps focused at a single depth, or it may provide a set of sweeps each using a different aperture in order to create a matrix of time traces that can be post-processed to provide an image that is sharp at all depths.

Therefore, in the process described with respect to FIG. 11, a processor, which in this example is the combination of CPU 312 and FPGA 306, identifies a number indicating an aperture size, generates a plurality of responses, which in this example is time traces 1106, from the transducers 301, and then processes the responses to produce image data. In this example the responses are generated by steps carried out by the FPGA: selecting a set of transducers (which set may be contiguous or non-contiguous, and the number of selected transducers being equal to the identified number), and sending a signal to each switch connected to a selected transducer instructing it to connect the transducer to the communications channel, which in this example is an instruction to close. The FPGA then sends instructions to fire the selected transducers, such that a pulse is provided to each transducer via the communications channel, and receives a single response.

In other embodiments all these steps could be carried out by a single processing chip, or separated out even further onto more chips.

FIG. 12

The equations used by CPU 312 during post-processing are shown in FIG. 12. A full description of the algorithm and its derivation can be found in United Kingdom Patent No. 2 512 115. Equations used in this process are shown in FIG. 12.

As discussed with reference to FIG. 7, equation 705, which is to be solved to obtain the image data from the time traces is:

$$y = Hx + n$$

where y is the time traces 702, x is the field of scatterers 701 being imaged, H is a blurring matrix 703, and n is a noise component 704. Given that y is known, H is known, and n can be modelled, we can arrive at an estimate for x.

The algorithm used finds the maximum a posteriori estimate for x, using equation 1201:

$$\hat{x} = (H^H \Sigma_n^{-1} H + S^{-2})^{-1} H^H \Sigma_n^{-1} y$$

where S is the echogenicity of x and $\Sigma_n$ is the co-variance of the noise. The algorithm iterates between improving point estimates of S and $\Sigma_n$ and improving the estimate of equation 1201.

The kth iteration of the algorithm can be written as equation 1202:

$$m_k = (H^H \Sigma_{n,k}^{-1} H + S_k^{-2})^{-1} H^H \Sigma_{n,k}^{-1} y$$

where $H^H$ is the Hermitian transpose of H.

The algorithm starts with the initial estimate 1203:

$$m_0 = (H^H H + \eta I)^{-1} H^H y$$

where η is a constant. A value of 0.3 for η has been found to be effective but other values can be used.

Since H is a large, non-sparse matrix, the calculation of $H^H$ is non-trivial. Therefore this calculation is done in the lateral K-time domain by applying a Fourier transform to H and considering a plurality of sub-matrices. These are combined and transformed back to the lateral domain. The matrix $H^H$ is then stored for use. Thus the initial estimate 1203 is obtained only from stored matrices and variables.

The initial estimate 1203 is used to update estimates for $S_k$ and $\Sigma_{n,k}$, and these estimates are used to update the estimate of equation 1202 ($m_k$). In this embodiment, the Conjugate Gradients algorithm is used to calculate equation 1202. A pre-conditioner P is used as shown in equation 1204:

$$(H^H \Sigma_{n,k}^{-1} H + S_k^{-2}) P^{-1} P m_k = H^H \Sigma_{n,k}^{-1} y$$

Using equation 1205, which has already been calculated in the initial estimate 1203, as the preconditioner, has been shown to improve the convergence of the algorithm:

$$P^{-1} = (H^H H + \eta I)^{-1}$$

Other methods of estimating equation 1202 may also be used.

Once an estimate for equation 1202 has been found, the estimates for $S_k$ and $\Sigma_{n,k}$ are updated and the process continues iteratively until satisfactory convergence is reached.

Thus an initial approximation 1201 ($m_0$ is made that is dependent only upon the blurring matrix 703 (H) and the time traces 702 (y). The value of x is then estimated by performing an iterative process, each iteration including performing the Conjugate Gradients algorithm using a preconditioner derived from the blurring matrix 703.

Other methods of solving the inverse matrix problem or estimating the image matrix, and other methods of post-processing may be used.

Figure 13A:
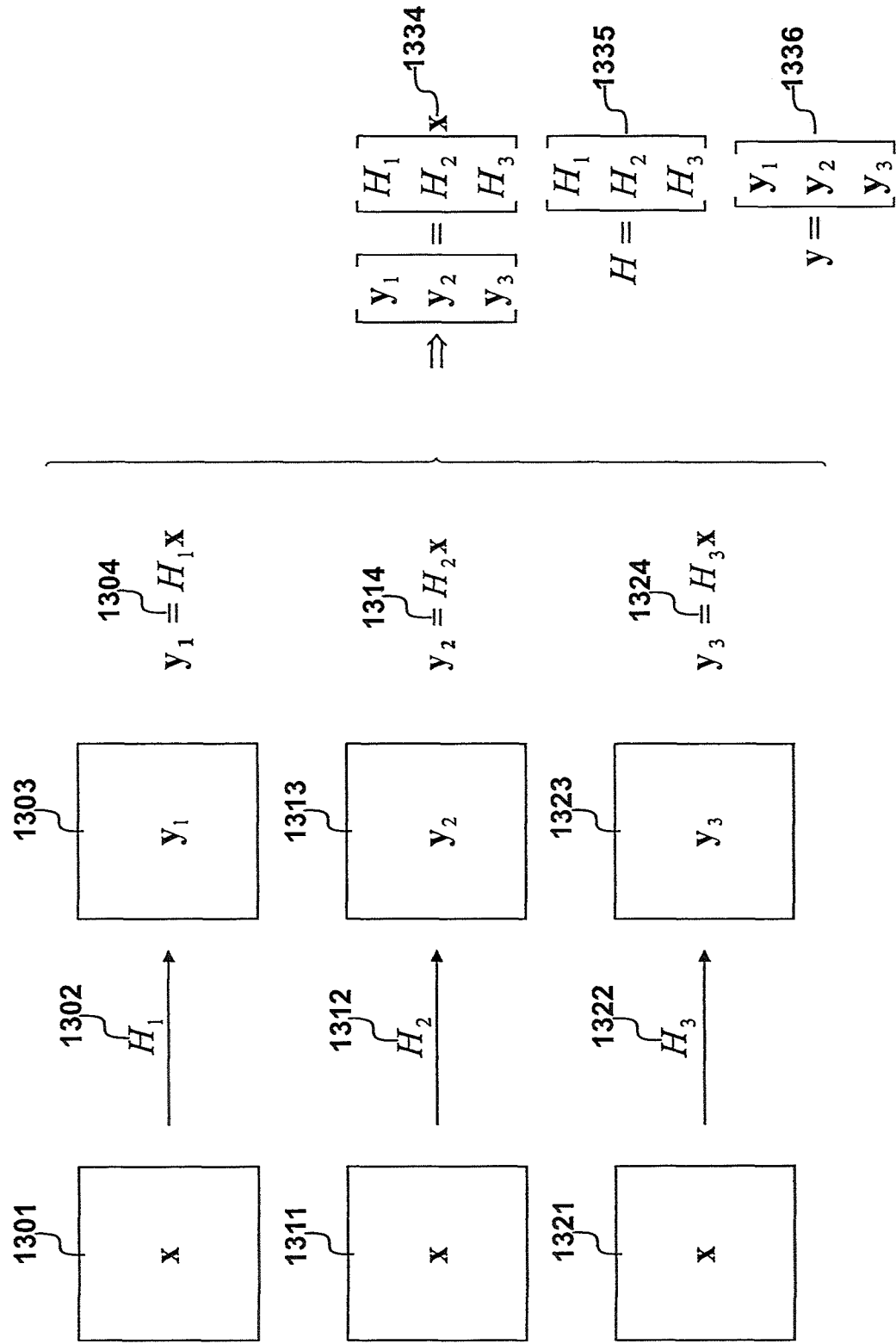

FIGS. 13*a* and 13*b*

Equation 705 considers the solution of a single matrix of time traces (setting aside the noise component):

$$y = Hx$$

However, as described with reference to FIG. 11, the ultrasound apparatus described herein can be used to create a set of time trace matrices, each having a different aperture. For example, the probe may sweep using an aperture of 4 elements, then an aperture of 8 elements, then an aperture of 16 elements.

In a traditional ultrasound probe, each transducer has its own channel, and therefore a single pulse results in a response from each transmitter that has been instructed to fire. For example, if eight transducers have been instructed to fire, then eight responses are received. These are generally subjected to a delay-and-sum process, and the output from the analog front end is a matrix of eight traces. Each step along the array produces another one of these matrices, and they are combined at the end of the sweep to form the full time traces matrix that is post-processed.

By contrast, in the invention herein described, a single pulse results in a single response, because all the transducers 301 are connected to a single communications channel 416. Therefore when the traces are combined at the end of the sweep to form time traces 1106, this is a smaller matrix than is produced by a traditional probe.

However, when the same scatterers are imaged a plurality of times, it is done using a probe with different characteristics (caused by the change in aperture) each time. This can be modelled as shown in the example in FIG. 13a, in which three sweeps are carried out.

First, a sweep using four elements is carried out, which images the shallow scatterers. This can be modelled as follows: matrix 1301 (x) representing the entire field of scatterers is transformed by a first blurring matrix 1302 ($H_1$) into first time traces 1303 ($y_1$). This is represented by equation 1304:

$$y_1 = H_1 x$$

Next, a sweep using eight elements is carried out, which images the medium-depth scatterers. This can be modelled as follows: the matrix 1311 (x) representing the scatterers is transformed by a second blurring matrix 1312 ($H_2$) into second time traces 1313 ($y_2$). This is represented by equation 1314:

$$y_2 = H_2 x$$

Finally, a sweep using sixteen elements is carried out, which images the deep scatterers. This can be modelled as follows: the matrix 1321 (x) representing the scatterers is transformed by a third blurring matrix 1322 ($H_3$) into third time traces 1323 ($y_3$). This is represented by equation 1324:

$$y_3 = H_3 x$$

Even though the blurring matrices 1302, 1312 and 1313 are smaller than the matrices produced by a traditional ultrasound probe, solving each of equations 1304, 1314 and 1324 individually would geometrically increase the amount of computation required. However, given that the field of scatterings 1301 being imaged remains the same, these equations can be combined into a single equation 1334:

$$\Rightarrow \begin{bmatrix} y_1 \\ y_2 \\ y_3 \end{bmatrix} = \begin{bmatrix} H_1 \\ H_2 \\ H_3 \end{bmatrix} x$$

Therefore the individual time trace matrices and the individual blurring matrices can be combined to form larger matrices which can be considered as the blurring matrix H and the time traces y in equation 705; equations 1335 and 1336 are:

$$H = \begin{bmatrix} H_1 \\ H_2 \\ H_3 \end{bmatrix}, y = \begin{bmatrix} y_1 \\ y_2 \\ y_3 \end{bmatrix}$$

Substituting equations 1335 and 1336 into the initial estimate 1203 gives equations 1337 and 1338:

$$H^H H = [H_1^H \ H_2^H \ H_3^H] \begin{bmatrix} H_1 \\ H_2 \\ H_3 \end{bmatrix} = [H_1^H H_1 + H_2^H H_2 + H_3^H H_3]$$

$$H^H y = [H_1^H \ H_2^H \ H_3^H] \begin{bmatrix} y_1 \\ y_2 \\ y_3 \end{bmatrix} = [H_1^H y_1 + H_2^H y_2 + H_3^H y_3]$$

Thus the matrix $H^H H$ is created by summing the individual matrices $H_1^H H_1$ and so on, and the matrix $H^H y$ is created by summing the matrices $H_1^H y_1$ and so on. These are relatively computationally-inexpensive calculations, and once they are done, the process described with respect to FIG. 12 can be used to post-process the combination of time traces for any number of sweeps, using little more processing power than was needed for one sweep.

The end result of this is that an image can be produced that is sharp at any depth, as opposed to the output from a traditional probe, which is only focused at one depth, and comparable to modern synthetic beam forming techniques that require a substantial amount of acquisition hardware. Further, because the apparatus herein described uses less circuitry (as was described with reference to FIG. 3), it uses less power. This allows the manufacture of an inexpensive, portable probe that produces high-quality images.

Extending the example described above to any number of sweeps (n) leads to the following equations. The initial estimate 1341 is:

$$m_0 = ([H_1^H H_1 + H_2^H H_2 + \ldots + H_n^H H_n] + \eta I)^{-1} [H_1^H y_1 + H_2^H y_2 + \ldots + H_n^H y_n]$$

Similar derivations lead to the kth iteration of the algorithm, equation 1342:

$$m_k = \left( \left[ H_1^H \sum_{n,k,1}^{-1} H_1 + H_2^H \sum_{n,k,2}^{-1} H_2 + \ldots + H_n^H \sum_{n,k,n}^{-1} H_n \right] + S_k^{-2} \right) - 1$$
$$\left[ H_1^H \sum_{n,k,1}^{-1} y_1 + H_2^H \sum_{n,k,2}^{-1} y_2 + \ldots + H_n^H \sum_{n,k,n}^{-1} y_n \right]$$

where $\Sigma_{n,k-1,j}$ is the jth (diagonal matrix) block of the block diagonal matrix $\Sigma_{n,k-1}$.

Equation 1342 can be solved in the same way as equation 1202, where the Conjugate Gradients algorithm is preconditioned with the matrix 1343:

$$P^{-1} = ([H_1^H H_1 + H_2^H H_2 + \ldots + H_n^H H_n] + \eta I)^{-1}$$

Again, other methods of post-processing the combination of time traces produced by a plurality of sweeps at different apertures may be used.

Thus a processor, which in this example is the combination of CPU 312 and FPGA 306, identifies a first and a second aperture size, and uses them to generate a first plurality of responses and a second plurality of responses from the transducers 301. The processor produces image data by 10 processing the first and the second plurality of responses together. This can be done by first retrieving a first blurring matrix, which in this example is matrix 1302, and a second blurring matrix, which in this example is matrix 1312, from memory, which in this example may be memory 313 or may be memory on a connected device, such as tablet 104. The first plurality of 15 responses is combined to create a first response matrix, which in this example is time traces 1303, and the second plurality of responses is combined to create a second response matrix, which in this example is time traces 1313. An image matrix is then calculated using all of these matrices.

FIG. 14

Figure 14:
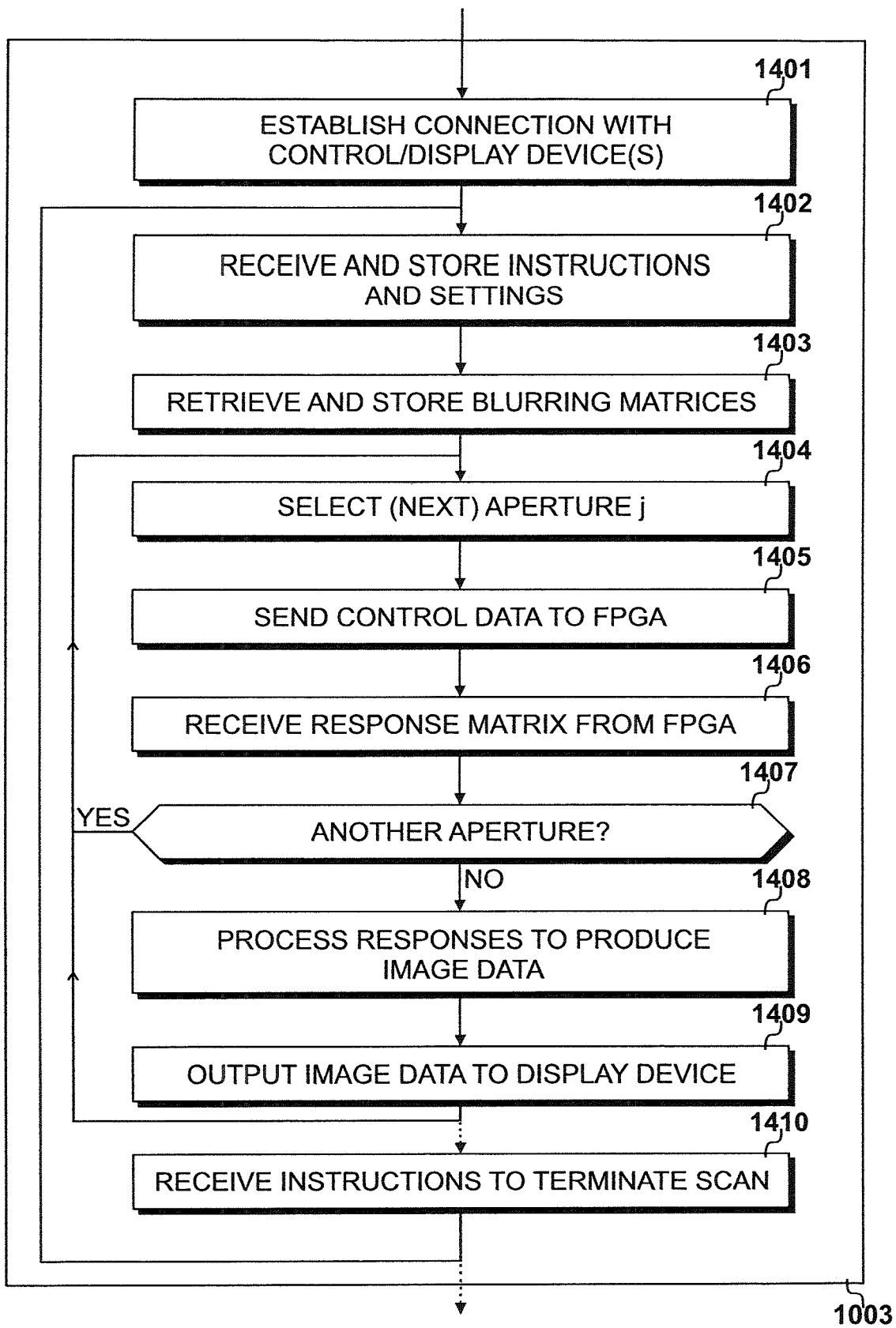
FIG. 14 details steps carried out during FIG. 10 to produce and output ultrasound images.

FIG. 14 details step 1003 at which ultrasound images are produced and output. In the description of this Figure and FIGS. 15 to 18, reference will be made to the overview shown in FIG. 11.

At step 1401 a connection is established with any control or display devices being used. In the embodiment described herein, tablet 104 acts as both the control and the display device and a connection is established using wireless interface 314. However, other arrangements are envisaged.

At step 1402 instructions and settings 1101 are received from the control device, which in this example is tablet 104. These include an indication of the aperture or apertures to be used in the scan. At step 1403 the blurring matrices and associated matrices for these apertures are retrieved from memory and stored, as will be detailed further with respect to FIG. 15.

At step 1404 the first required aperture is selected (this will be referred to as aperture j in the following Figures) and at step 1405 control data 1102 is sent to FPGA 306, instructing it to carry out a sweep using this aperture. At step 1405 a response matrix is received from FPGA, having performed the sweep. At step 1407 a question is asked as to whether there is another aperture to be used, and if this question is answered in the affirmative then control is returned to step 1404 and the next aperture is selected.

Alternatively, if the question asked at step 1407 is answered in the negative, then at step 1408 all the responses received at step 1406 are processed to produce image data, which is output to the display device at step 1409. Control is then returned to step 1404 and the first aperture is selected again.

Thus the iterations of step 1404 to 1409 carried out repeatedly produce a stream of image data that is output to the display device. Each iteration takes a fraction of a second, and therefore the experience of user 102 is of a smooth video stream as she moves probe 101 across the abdomen of patient 103.

While steps 1404 to 1409 have been written linearly, in fact a degree of threading occurs, so that the post-processing at step 1408 takes place while waiting for the responses from the FPGA at step 1406. This separation of tasks is appropriate to the speed and capability of currently-available chips, but in the future other arrangements may be more suitable.

Steps 1404 to 1409 are eventually interrupted by receiving instructions from the control device at step 1410 to terminate the scan. Step 1003 may then be over, or alternatively instructions to commence a new scan may be received at step 1402.

FIG. 15

Figure 15:
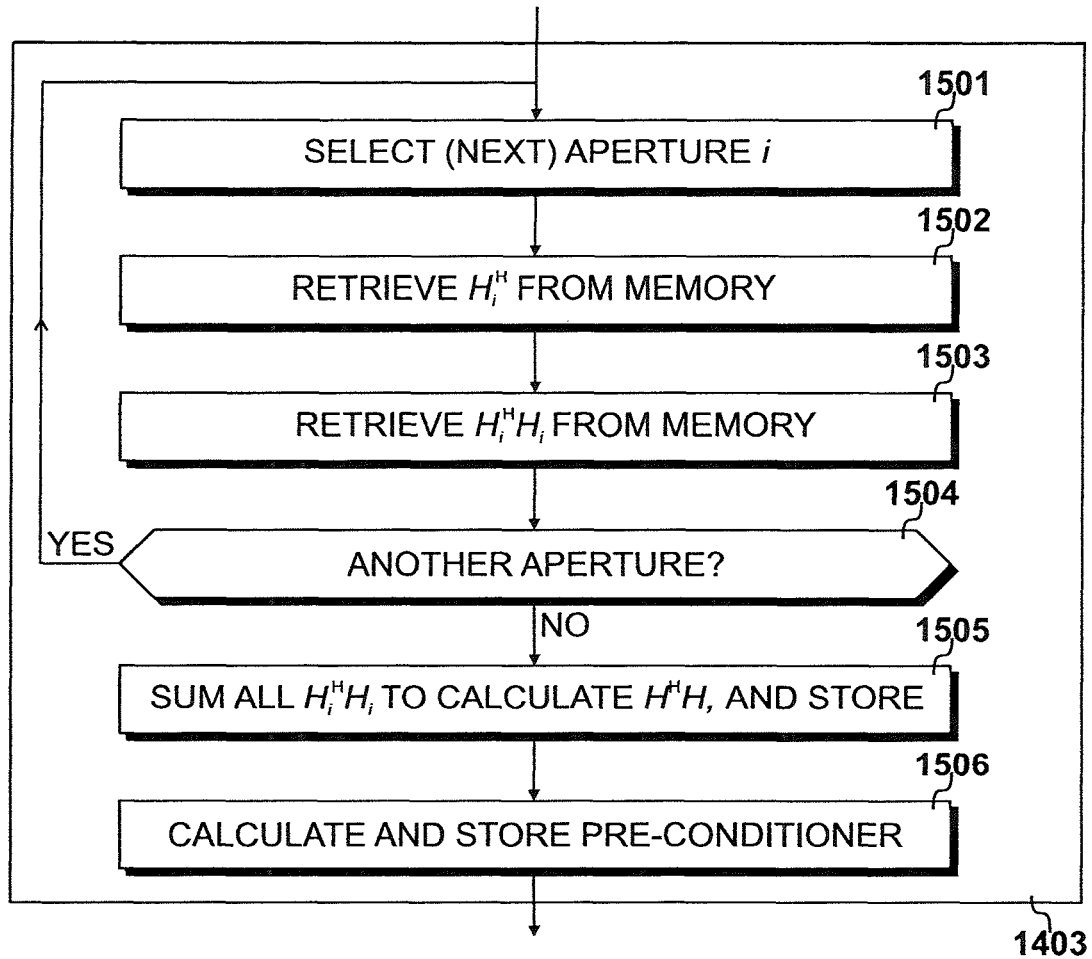
FIG. 15 details steps carried out during FIG. 14 to retrieve blurring matrices.

FIG. 15 details step 1403 at which the required blurring matrices are retrieved and stored.

As previously described, each aperture available to be selected by the user has an associated blurring matrix (H). This is obtained by scanning a known field of scatterers using an aperture of this size. Other aperture characteristics that may affect the blurring matrix are whether the aperture consists of contiguous elements or elements spaced apart, and so on. The blurring matrix may be obtained by recording a single pulse using the aperture into a known field of scatterers. Alternatively, an entire sweep may be carried out using the sweep characteristics, which include the startpoint, the step size, the edge characteristics and so on. This process is carried out before the probe is used, and may be considered a calibration process.

For each aperture, once a blurring matrix (H) has been stored, its Hermitian transpose ($H^H$) is calculated and stored, along with the product of the Hermitian transpose of the blurring matrix and the blurring matrix ($H^H H$).

These matrices may be stored in memory 313 of the probe. Alternatively, if memory space is an issue, they may be stored on the control device and provided along with instructions 1101, or they may be stored a network location and obtained via a wireless connection. They could also be stored on an external storage device that interfaces with probe 101, such as via a USB port.

FIG. 15 details the steps carried out at step 1403 to retrieve and store the appropriate matrices.

At step 1501 the first aperture indicated in instructions 1101 is selected, which is here labelled i. At step 1502 the Hermitian transpose of the blurring matrix for this aperture ($H_i^H$) is retrieved from memory 313 or from any other location where it is stored. At step 1503 the product of the Hermitian transpose of the blurring matrix and the blurring matrix ($H_i^H H_i$) is retrieved from memory. Both of these matrices are stored, and at step 1504 a question is asked as to whether there is another aperture indicated in instructions 1101. If this is answered in the affirmative then control is returned to step 1501 and the next aperture is selected.

If all the apertures have been considered, then at step 1505 all the matrices stored at the iterations of step 1503 are summed (as shown in equation 1337) to calculate the combined matrix $H^H H$, which is stored. This is the matrix that is used specifically for this combination of apertures. A scan using different apertures would have a different combined matrix $H^H H$.

At step 1506 the preconditioner shown at equation 1343 is calculated and stored. This uses the combined matrix $H^H H$, along with a predetermined constant q, set in this example as 0.3.

Thus, at the end of step 1403, all the matrices required to perform post-processing on the data have been stored.

FIG. 16

Figure 16:
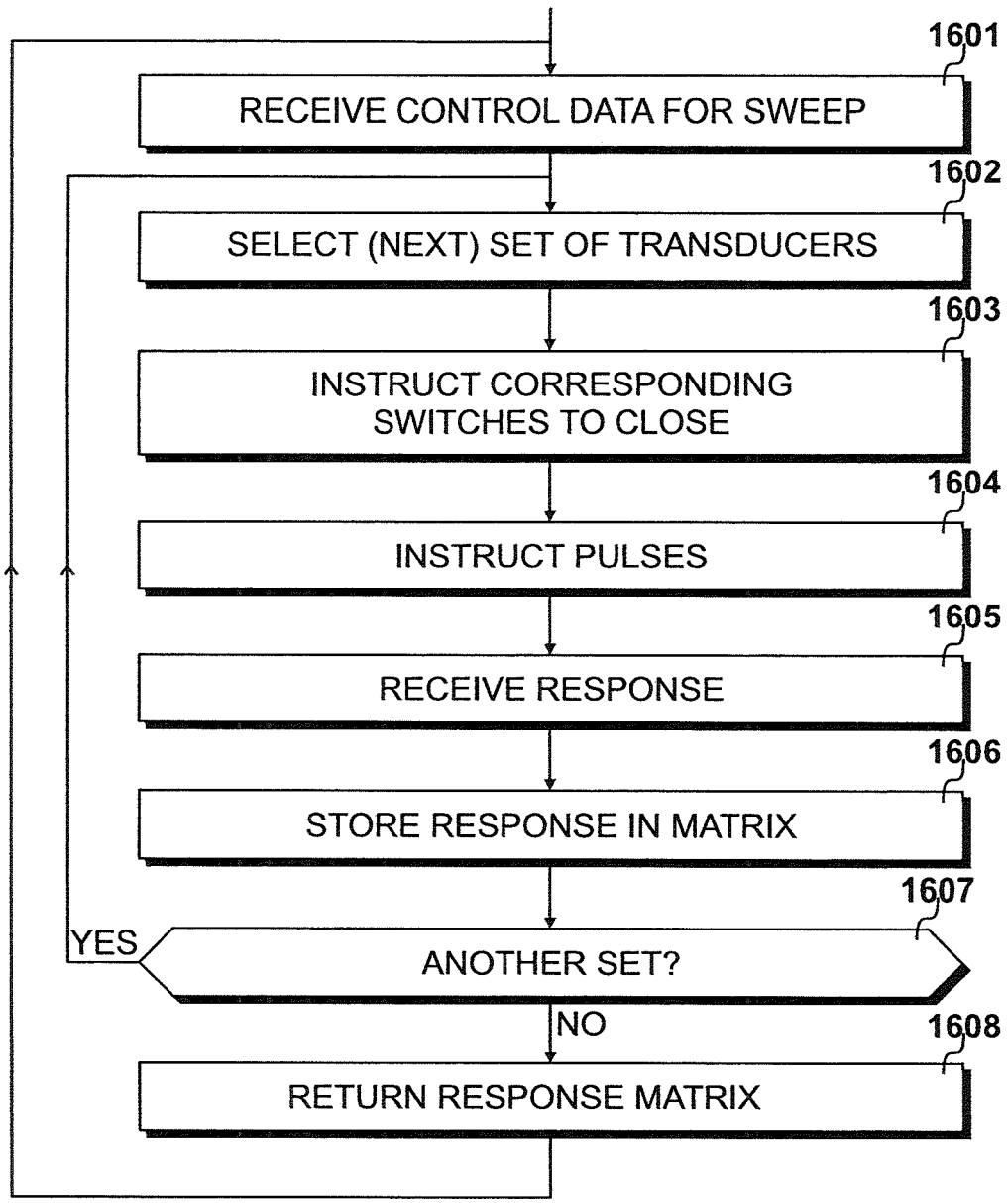
FIG. 16 details steps carried out by the FPGA shown in FIG. 3 to perform sweeps of the transducer array shown in FIG. 3.

FIG. 16 details steps carried out by FPGA 306 after receiving instructions sent by CPU 312 at step 1405. As previously described, this separation of processes, with the sweep being controlled by the FPGA while the CPU has overall control of the process and performs post-processing, is considered efficient based on the technology currently available. However, it is envisaged that these processes could be performed by a single chip or could be separated out onto more chips. The CPU and the FPGA can therefore be considered as a single processor that carries out all the steps required to perform the sweeps of the transducer array and perform the post-processing.

Returning to this specific embodiment, the FPGA receives control data 1102 at step 1601 instructing it to carry out a sweep of the transducer array. This control data includes aperture characteristics and sweep characteristics. At step 1602 a first set of transducers is selected according to these settings, and at step 1603 each switch corresponding to a selected transducer is instructed to close. This is done via aperture control process 310. At step 1604 instructions are sent to the pulser 307, via fire control process 309, to send a pulse via transmit/receive switch 305 to the switch array 303. This pulse passes through the closed switches only, and fires the selected transducers. A single response is received via transmit/receive switch 305 and analog front end 308 at step 1605, and at step 1606 this response is stored.

At step 1607 a question is asked as to whether there is another set of transducers in the current sweep, and if this question is answered in the affirmative then control is returned to step 1602 and the next set is selected. Alternatively, if the sweep is concluded then the response matrix created by repeated iterations of step 1606 is returned as time traces 1106 to CPU 312 at step 1608. The FPGA then awaits further control data at step 1601.

FIG. 17

Figure 17:
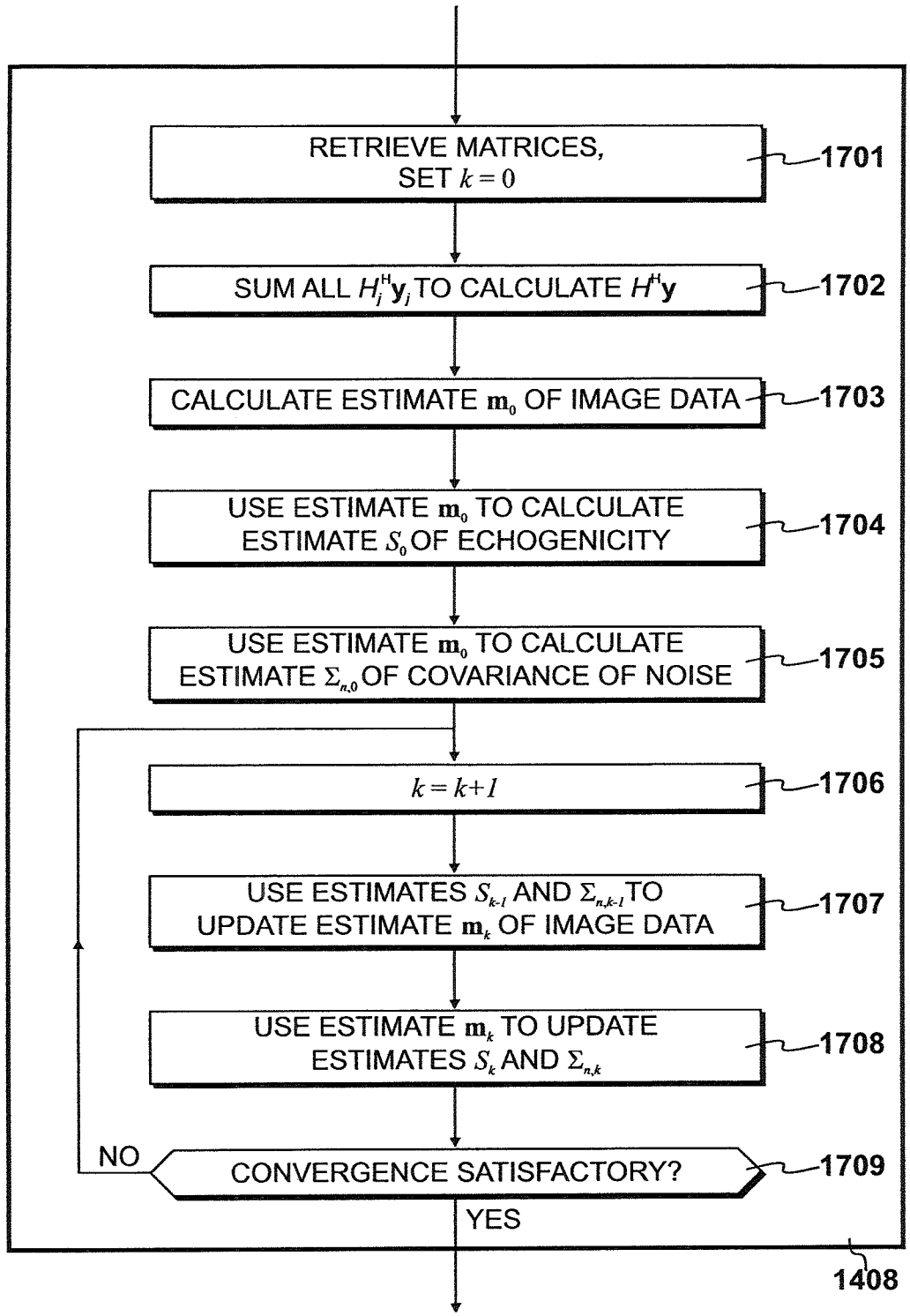
FIG. 17 details steps carried out during FIG. 14 to perform post-processing on ultrasound data.

FIG. 17 details step 1408, at which the time traces 1106 received by CPU 312 are processed to produce image data.

At step 1701 the process is initialised by retrieving the required 15 matrices from memory and setting the variable k to zero. The matrices retrieved include all the received time traces $y_j$, all the Hermitian transposes for the apertures $H_j^H$, the combined matrix $H^H H$, and the pre-conditioner $p^{-1}$.

At step 1702 the matrix $H^H y$ is calculated. This is done by, for each received time trace $y_j$, identifying the Hermitian transpose of the blurring matrix ($H_j^H$) corresponding to the aperture used to produce the time trace and calculating the product of these two matrices ($H_j^H y_j$). Once all of these products are calculated, they are summed to produce $H^H y$. Then at step 1703 the first estimate $m_0$ of the image data is generated, using equation 1341.

At step 1704 the estimate $m_0$ is used to calculate the first estimate $S_0$ of the echogenicity, using any appropriate method. At step 1705 the estimate $m_0$ is used to calculate the first estimate $\Sigma_{n,0}$ of the co-variance of the noise, using any appropriate method.

At step 1706 k is incremented by one and, at step 1707, what are now estimates $S_{k-1}$ and $\Sigma_{n,k-1}$ are used to update the estimate $m_k$ of the image data. As was described with reference to FIG. 13b, this step may be done using a convergence algorithm. In this embodiment, the Conjugate Gradients algorithm is used with the preconditioner $P^{-1}$. At step 1708 this new estimate $m_k$ is used to update the estimate $S_k$ of the echogenicity and $\Sigma_{n,k}$ of the covariance of the noise. At 1709 a question is asked as to whether the convergence of the process is satisfactory. If this question is answered in the negative then control is returned to step 1706, k is incremented by one and steps 1707 and 1708 are carried out again. If, however, the convergence is satisfactory at step 1709 then step 1408 is completed.

The last estimate $m_k$ of the mean of the distribution of the scatterer field, is used as the best estimate of the scatterer field, and is therefore output as image data at step 1408.

Thus the process described with respect to FIGS. 14 to 17 is a method of obtaining and outputting image data representing a field of scatterers. This method is suitable for use with ultrasound apparatus 101. However, other methods of post-processing may also be used, including other methods of solving the inverse matrix problem or estimating the image data.

FIG. 18

The apparatus described with respect to FIGS. 3 and 4a produces a stream of 2-dimensional images. The two axes are the transducer array, and the depth into the field of scatterers. Therefore, in order to produce a 3-dimensional image, a 2-dimensional transducer array is required. These are referred to in the art as 2D arrays.

Prior art 3D ultrasound apparatus are very expensive. They follow the standard model of one communications channel per transducer, with a large multiplexer. To fire and process a 16×16 aperture, which contains 256 elements, 256 analog front ends and 256 pulsers are required. Thus to be able to provide a usefully sized aperture, the circuitry must be very extensive.

Figure 18:
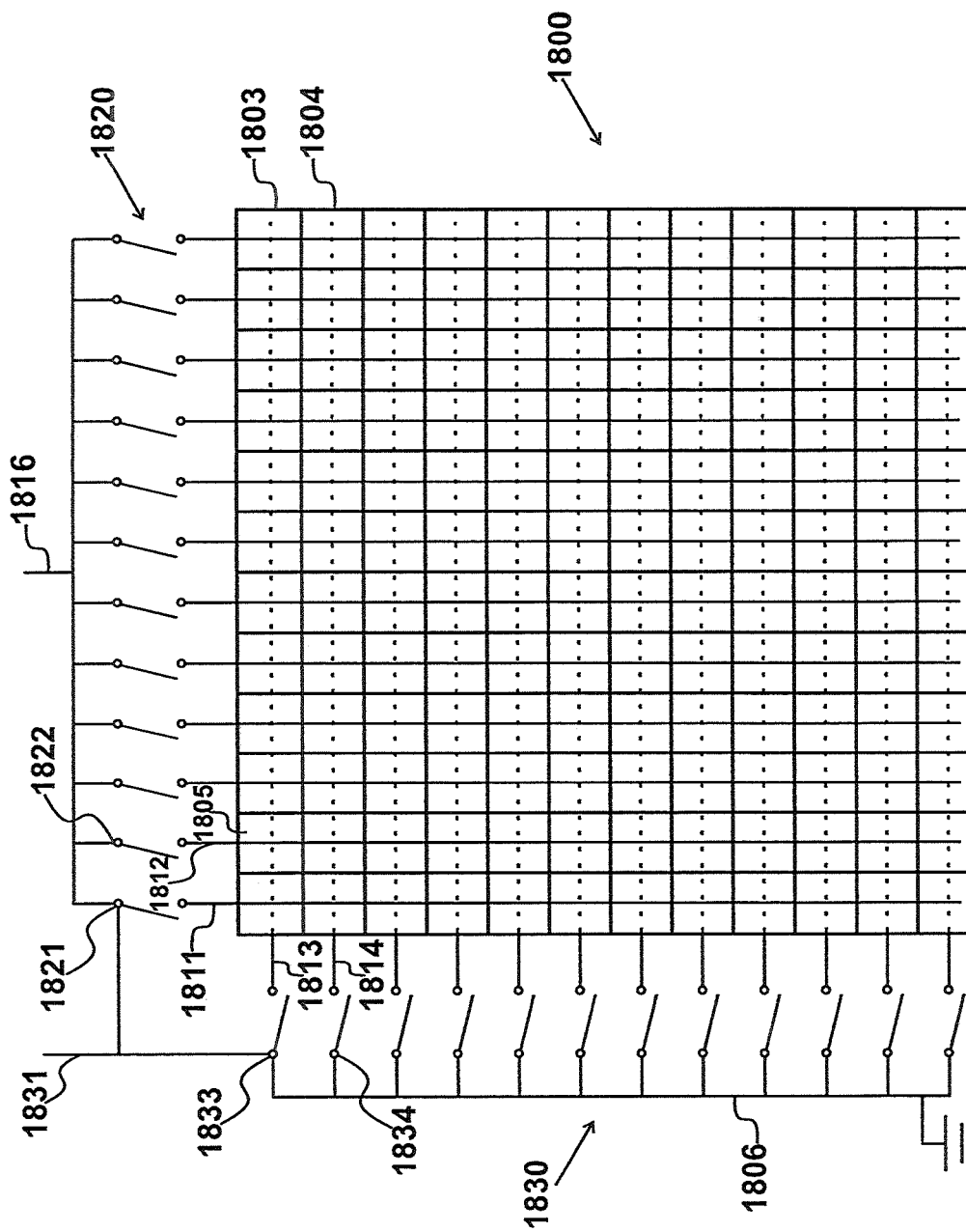
FIG. 18 illustrates a second embodiment of an ultrasound array suitable for use in the apparatus shown in FIG. 3.

FIG. 18 is a diagrammatic illustration of a second embodiment of the invention. It shows a 2D array that does not require extensive circuitry to run it. This array, together with the switches also shown in FIG. 18, can replace the transducer array 301 and switch array 303 in FIG. 3. The remainder of the circuitry shown in FIG. 3 remains the same.

Array 1800 uses the same principle as shown in FIG. 4a, that each transducer is connected to a single communications channel via a switch, such that a number of selected transducers can be fired using a single pulse, and a single response is received from the transducers.

Array 1800 has, for simplicity of illustration, only 144 transducer elements arranged in a 12×12 matrix, but a typical array would have many more transducers, for example 128×128. Any number of transducers that is possible. Further, the array does not need to be square; any suitable shape is envisaged.

In array 1800, each transducer in a column is connected via a single wire to one of an array 1820 of channel switches. Thus for example, each transducer in column 1801 is connected via wire 1811 to channel switch 1821. Each transducer in column 1802 is connected via wire 1812 to channel switch 1822, and so on. Each of the channel switches in array 1820 connects to a single communications channel 1816.

Wires 1811, 1812 and so on run across the top of the transducer elements. Underneath the elements, there are further wires connecting each transducer in a row to one of an array 1830 of ground switches. Thus each transducer in row 1803 is connected via wire 1813 to ground switch 1833, each transducer in row 1804 is connected via wire 1814 to ground switch 1834, and so on. Each of the ground switches is connected via wire 1806 to ground.

Each of the switches in array 1820 and in array 1830 is connected via a control channel to fire control process 309 on FPGA 306. This connection is shown for simplicity in FIG. 18 as a single line 1831, but should be understood to be a set of individual control channels such as is shown in FIGS. 4a to 4c, such that each switch can be independently opened and closed.

Thus each transducer in array 1800 is uniquely addressed by a channel switch and a ground switch. Thus for example, element 1805 is addressed by channel switch 1822 and ground switch 1833. Each transducer can therefore be turned "on" by closing the two switches that address it. For example, if switches 1822 and 1833 are closed before a pulse is provided via communications channel 1816, this pulse will be provided to each transducer in column 1802. However, of these transducers, only transducer 1805 is connected to ground (via switch 1833).

If the transducer array can be constructed such that there is no interference between transducers, then and therefore only transducer 1805 fires. The other transducers in column 1802 will not fire, nor the transducers in row 1813. Thus a notional square or rectangular aperture can be created by closing one or more adjacent channel switches in array 1820 and one or more adjacent ground switches in array 1830.

However, given the nature of the impedance network that is created by the described addressing scheme, there is potential set up across transducer elements outside of the addressed rectangle. Therefore the aperture shape created by closing adjacent channel switches and adjacent ground switches is in fact a cross shape, where the addressed transducers fire more strongly than the other transducers in the relevant rows and columns. The remaining transducers fire very weakly. As the array increases in size, the potentials across the tranducers outside the cross shape tends to zero, and can therefore be disregarded. An array size of over 128×128 has been found to be a reasonable size.

Because this cross shape is consistently produced, it is an acceptable aperture shape and can therefore be used as effectively as the ideal square aperture. The blurring matrices for the various apertures sizes produced by the 3-D probe are generated and stored in the same way as when using a 2-D probe.

Therefore a 2D aperture, either of a square or a cross shape, can be created by closing one or more channel switches in array 1820 and one or more ground switches in array 1830. A pulse is sent down communications channel 1816 through the closed channel switches to the addressed transducers, and a single response is returned from these transducers via communications channel 1816. Thus the transducer array 1800 and switch arrays 1820 and 1830 can be used in place of transducer array 301 and switch array 303 in the apparatus shown in FIG. 3. No further circuitry is needed, meaning that the only increase in cost relates to the additional transducer elements, switches and wires required. Thus a 3D ultrasound probe can be produced that is inexpensive and can be run portably using a battery.

FIG. 19

Figure 19:
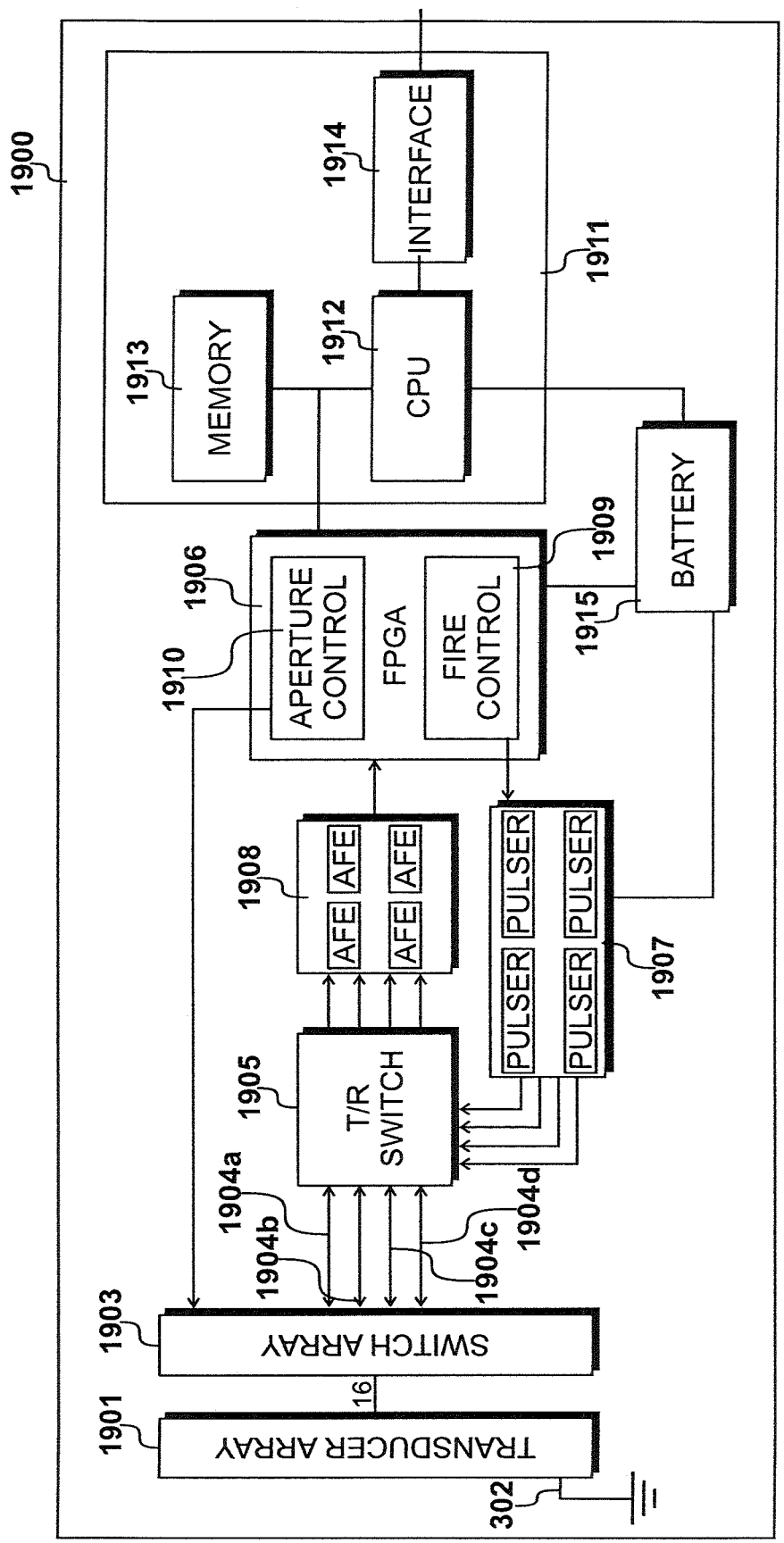
FIG. 19 illustrates a third embodiment of the ultrasound apparatus.
Figure 20:
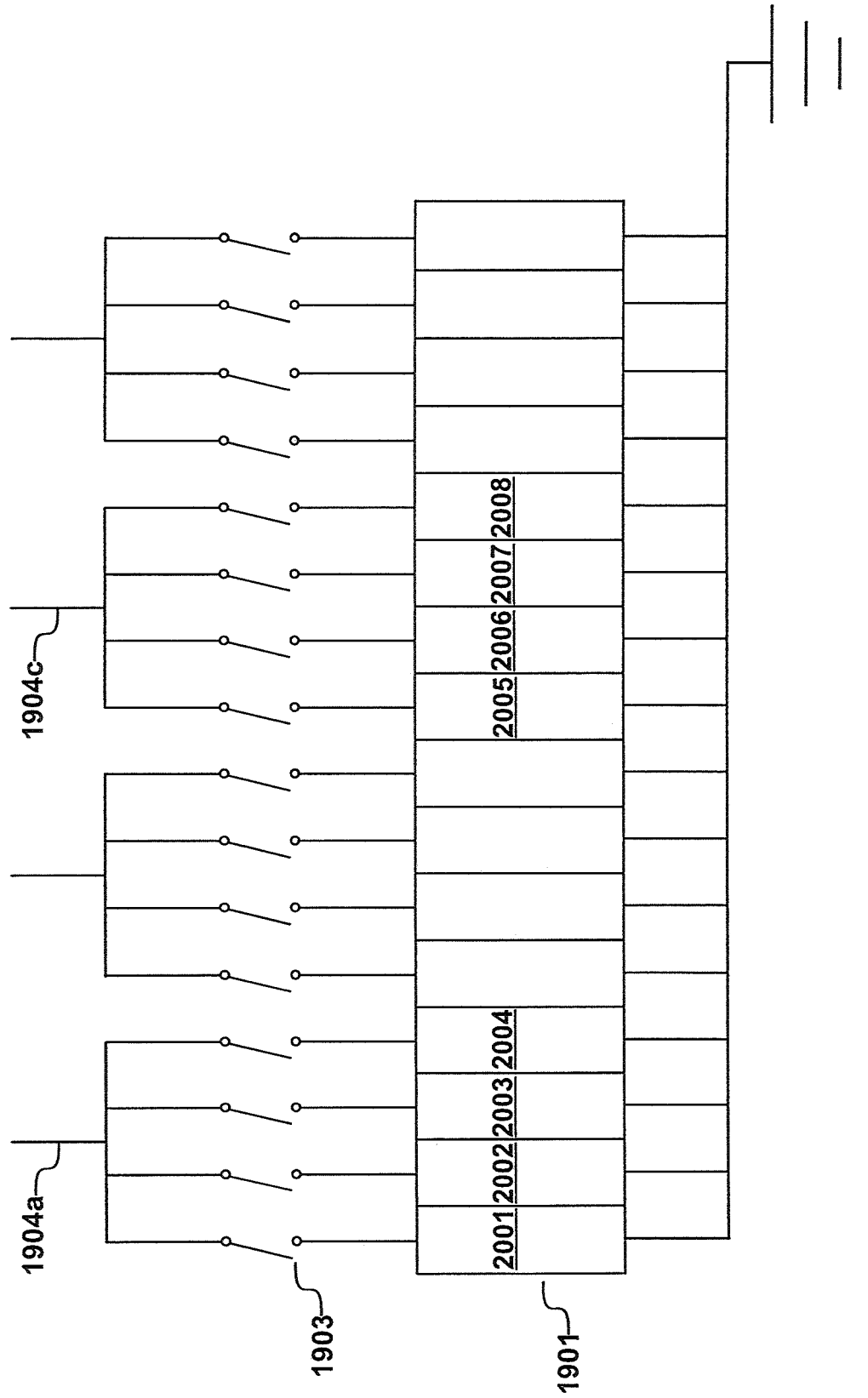
FIG. 20 is a diagrammatic representation of a transducer array shown in FIG. 19.

A third embodiment of the invention is shown in FIGS. 19 and 20. While the array shown in FIG. 18 can be used with the ultrasound apparatus shown in FIG. 3, this third embodiment requires additional apparatus. Thus, a probe 1900 is diagrammatically illustrated in FIG. 19. This includes a transducer array 1901, each of the transducers being connected to ground as shown at 1902, and a switch array 1903. In this embodiment there are 16 connections between the switch array and the transducer array, one for each transducer element (as will be described below, the array in this example is small for ease of illustration). The switches are each connected to aperture control process 1910 on FPGA 1906. In addition, four communication channels 1904a, 1904b, 1904c and 1904d connect the switches 1903 to a transmit/receive switch 1905, which may be a set of switches or a single switch matrix. These are connected to four analog front ends, indicated collectively at 1908, and to four pulsers, indicated collectively at 1907.

Probe 1900 also includes a processing unit 1911 that includes a CPU 1912, memory 1913 and wireless interface 1914. A battery 1915 provides power to the various components of probe 1900.

The components of probe 1900 are largely similar to those of probe 101. In particular the processing unit 1911 is substantially identical to processing unit 311, and FPGA 1906, with its aperture control 1910 and fire control 1909, is substantially identical to FPGA 306. Battery 1915 may be configured to provide more power than battery 315, but is otherwise similar.

The differences between probe 1900 and probe 101 are the addition of the extra analog front ends and pulsers, the larger transmit/receive switch 1905, and the four communication channels linking the transducer array, via the switches, to the rest of the circuitry.

FIG. 20

FIG. 20 is a diagrammatic illustration of transducer array 1901 and switch array 1903. In example of FIGS. 19 and 20, only 16 transducers are shown, for simplicity. However, in a typical arrangement there would be more transducers, for example 128.

In this example, the 16 transducers are grouped into sets of four. For example, the first set of transducers, transducers 2001, 2002, 2003, and 2004, are connected via their respective switches to first communications channel 1904a. Again for simplicity, the individual control channels to the switch array 1903 are not shown, but they are similar to those shown in FIGS. 4a and 4c. Like in the previous two embodiments, each switch is individually controlled to open and close, and the first set of transducers is connected to a single communications channel 1904a, down which the pulse is fired and via which the response from the transducers is received. The difference between this embodiment and the first embodiment is the addition of additional sets of transducers, each connected to a further communications channel.

The transducer array shown in FIG. 20 allows more than one sweep to be carried out simultaneously, but does not use as much circuitry as a traditional ultrasound probe. In use, FPGA 1906 carries out simultaneous sweeps by selecting two sets of transducers to fire. These sets would need to be far enough apart from each other such that there would not be any interference. Thus, for example, the first set selected could be transducers 2001 to 2004, and the second set could be transducers 2005, 2006, 2007 and 2008, which are connected via their respective switches to control channel 1904c. Aperture control process 1910 instructs the switches for all of these transducers to close, and then sends pulses, via the pulses 1907, down channels 1904a and 1904c.

Separate responses are received via analog front ends 1908, and separately stored. The apertures are then stepped across by one transducer and the process continues. When the second sweep that started with the second set of transducers reaches the right-hand edge of the transducer array 1901, it will start again at the left-hand edge, ie transducer 2001. Thus, in the time it would take the first embodiment to do one sweep, two response matrices representing two sweeps will have been stored.

In this third embodiment the post processing discussed with respect to FIGS. 12 to 17 is carried out slightly differently to account for the fact that the responses from some apertures will be spread between two communications channels. In addition, the sweep's edge characteristics need to be chosen carefully. However, the basic process is similar.

Manufacture of the Transducer Arrays

Three embodiments have been described herein of ultrasound apparatus. In each one, there is a plurality of transducers, each of which is connected to a communications channel via a switch, such that when a set of the transducers is fired, a single response is provided to a processing unit via the communications channel. In the third embodiment, there are further such sets of transducers and switches and further communications channels. In the second embodiment, there is in addition a set of switches via which the transducers are connected to ground; in this embodiment, more than one transducer is connected to each switch, whereas in the first and third embodiments each switch is connected to a single transducer.

A fourth embodiment is envisaged which combines the second and third embodiments, that is, a 2-D transducer array in which the switches are arranged in two sets. Further embodiments not described herein are also envisaged, in which transducers are connected via switches to a single communications channel.

For each of these embodiments, the transducer array may be manufactured in any suitable way. In the current embodiment, the array is manufactured by printing elements and wires onto a plastic substrate. Other manufacturing options include: golding the surface of a piece of ceramic piezoelectric transducer and defining the elements by sawing fine slits; attaching very small pieces of transducer to a substrate and back filling; and so on.

The switches may be any switch that can be opened and closed to provide a link between two ends of a communications channel. In these embodiments the switches are small hardware switches, but they could also be implemented in software.

As previously discussed, the embodiments described herein include a probe casing that contains all of the ultrasound apparatus, with a wireless interface to a control device and/or a display device. The casing can be of any shape suitable to accommodate the circuitry and fit into a user's hand. However, other embodiments are envisaged where certain elements of a circuitry are found within the control device or the display device.

The invention claimed is:
1. An ultrasound apparatus comprising
   a first plurality of transducers,
   a first plurality of switches,
   a single pulser,
   a single receiver, and
   a processing unit, wherein:
      each of said first plurality of transducers is connected to said single pulser and to said single receiver via one of said first plurality of switches and via a single communication channel,
      said processing unit includes a memory and a processor,
      said processing unit is connected to said pulser and to said receiver, and
      said processor is configured to:
         identify a first number that indicates a first aperture size,
         provide instructions to generate a first plurality of responses from said first plurality of transducers,
         process said first plurality of responses to produce image data, and
         generate each of said first plurality of responses by:
            selecting a first set of transducers from said first plurality of transducers,
               wherein the first set may be contiguous or non-contiguous, the number of transducers in said first set being equal to said first number,
            identifying a first set of switches from said first plurality of switches comprising the switches connected to each of said first set of transducers,
            for each switch of said first set of switches, sending a signal instructing said each switch to connect its respective transducer to said single communication channel,
            sending instructions to the single pulser to simultaneously fire each of said first set of transducers, such that a single pulse is provided simultaneously to each of said selected transducers via said single communication channel to generate said each response, and
            receiving said each response via said single communication channel and said single receiver, said each response being a combination of outputs of the first set of transducers.

2. An ultrasound apparatus according to claim 1, wherein said processor is configured to process said first plurality of responses by: in response to said first aperture size, selecting and retrieving a blurring matrix from the memory; combining said first plurality of responses into a response matrix; and calculating an image matrix using said response matrix and said blurring matrix.

3. An ultrasound apparatus according to claim 1, wherein said processor is further configured to:
   identify a second number that indicates a second aperture size; and
   provide instructions to generate a second plurality of responses from said transducers, wherein each of said second plurality of responses is generated from a second set of transducers from said first plurality of transducers, wherein the second set may be contiguous or non-contiguous, the number of transducers in said second set being equal to said second number;
   wherein said processor is configured to produce said image data by processing said first plurality of responses and said second plurality of responses together.

4. An ultrasound apparatus according to claim 3, wherein said processor is configured to process said first plurality and second plurality of responses by:
   retrieving a first blurring matrix from memory, selected in response to said first aperture size;
   retrieving a second blurring matrix from memory, selected in response to said second aperture size;
   combining said first plurality of responses to create a first response matrix;
   combining said second plurality of responses to create a second response matrix; and
   calculating an image matrix using said first and said second response matrices and said first and said second blurring matrices.

5. An ultrasound apparatus according to claim 4, wherein said processor is configured to calculate the image matrix by estimating the sum of:
   the product of: a matrix combining both said first and said second response matrices and a matrix combining the inverse of both said first and said second blurring matrices; and
   a noise component.

6. An ultrasound apparatus according to claim 5, wherein said processor is configured to carry out said estimation by performing an iterative algorithm, wherein each iteration includes performing a Conjugate Gradients algorithm using a pre-conditioner derived from both said first and said second blurring matrices.

7. An ultrasound apparatus according to claim 1, further comprising a transmit/receive switch connected to said single communication channel, wherein:
   said receiver is provided by a first analog front end;
   said first analog front end and said single pulser are connected to said transmit/receive switch;
   said processor is connected to said first analog front end and said single pulser;
   said single pulser is configured to receive said instructions from said processor to fire each of said first set of transducers; and
   said first analog front end is configured to provide said single response to said processor.

8. An ultrasound apparatus according to claim 7, further comprising
   a second plurality of transducers,
   a second plurality of switches,
   a second communication channel,
   a second analog front end, and
   a second pulser, wherein:
      each of said second plurality of transducers is connected to said second communication channel via one of said second plurality of switches,
      said second communication channel is connected via said transmit/receive switch to said second analog front end and said second pulser, and
      said processor is configured to generate each of said first plurality of responses by carrying out the further steps of:
         selecting a second set of transducers from said second plurality of transducers,
            wherein the second set may be contiguous or non-contiguous, the number of transducers in said second set being equal to said first number;

identifying a second set of switches from said second plurality of switches comprising the switches connected to each of said second set of transducers;

for each switch of said second set of switches, sending a signal instructing said each switch to connect its respective transducer to said second communication channel;

sending instructions via said second analog front end to fire each of said second set of transducers via said second communication channel, simultaneously with the firing of said first set transducers; and receiving a second response via said second communication channel, said second response being the combination of outputs of said second set of transducers.

9. An ultrasound apparatus according to claim 1, wherein each of said first plurality of switches is connected to only one of said first plurality of transducers.

10. An ultrasound apparatus according to claim 1, further comprising a third plurality of switches, wherein said first plurality of transducers are arranged in a two-dimensional array, thus creating rows and columns of transducers, each row of transducers is connected to said single communication channel via one of said first plurality of switches, and each column of transducers is connected to ground via one of said third plurality of switches such that each of said first plurality of transducers can be uniquely addressed by one of said first plurality of switches and one of said third plurality of switches.

11. An ultrasound apparatus according to claim 1, wherein said processing unit further comprises a communication interface, and said processor is further configured to output, via said communication interface, an image derived from said image data.

12. A method of producing ultrasound image data using an ultrasound apparatus comprising a first plurality of transducers, a first plurality of switches, a single pulser, a single receiver, and a processing unit, wherein each of said first plurality of transducers is connected to said single pulser and to said single receiver via one of said first plurality of switches and via a single communication channel, comprising the steps of:

identifying a first number that indicates a first aperture size;

generating a first plurality of responses from a said first plurality of transducers;

processing said first plurality of responses to produce image data; and outputting said image data;

wherein said step of generating each of said first plurality of responses comprises the steps of:

selecting a first set of transducers from said first plurality of transducers, wherein the first set may be contiguous or non-contiguous, and the number of transducers in said first set being equal to said first number;

identifying a first set of switches from said first plurality of switches comprising the switches connected to each of said first set of transducers;

for each switch of said first set of switches, sending a signal instructing said each switch to connect its respective transducer to said single communication channel, at said single pulser, sending a single pulse to said first set of transducers via said single communication channel, such that the single pulse is received simultaneously by said first set of transducers to generate said each response;

receiving said each response from said first set of transducers via said single communication channel and via said single receiver; and storing said each response.

13. A method according to claim 12, wherein said step of processing said first plurality of responses comprises the steps of: in response to said first aperture size, selecting and retrieving a blurring matrix; combining said first plurality of responses into a response matrix; and calculating an image matrix using said response matrix and said blurring matrix.

14. A method according to according to claim 12, further comprising the steps of:

identifying a second number that indicates a second aperture size;

generating a second plurality of responses from said transducers, wherein each of said second plurality of responses is generated from a second set of transducers from said first plurality of transducers, which set may be contiguous or non-contiguous, the number of transducers in said second set being equal to said second number;

processing said first plurality of responses and said second plurality of responses together to produce said image data.

15. A method according to claim 14, wherein said step of processing said first plurality and second plurality of responses comprises the steps of:

selecting a first blurring matrix in response to said first aperture size;

selecting a second blurring matrix in response to said second aperture size;

combining said first plurality of responses to create a first response matrix;

combining said second plurality of responses to create a second response matrix; and calculating an image matrix using said first and said second response matrices and said first and said second blurring matrices.

16. A method according to claim 15, wherein said step of calculating said image matrix comprises estimating the sum of:

the product of: a matrix combining both response matrices and a matrix combining the inverse of both said first and said second blurring matrices; and a noise component.

17. A method according to claim 16, wherein said estimating step comprises performing an iterative algorithm, wherein each iteration includes performing a Conjugate Gradients algorithm using a pre-conditioner derived from both said first and said second blurring matrices.

18. A method according to claim 12, wherein said ultrasound apparatus further comprises a second plurality of transducers, a second plurality of switches, a second communication channel, a second analog front end, and a second pulser, wherein each of said second plurality of transducers is connected to said second communication channel via one of said second plurality of switches, and said second communication channel is connected via a transmit/receive switch to said second analog front end and said second pulser, and wherein said step of generating said first plurality of responses further comprises the steps of:

selecting a second set of transducers from said second plurality of transducers, wherein the second set may be contiguous or non-contiguous, the number of transducers in said second set being equal to said first number;

identifying a second set of switches from said second plurality of switches comprising the switches connected to each of said second set of transducers;

for each switch of said second set of switches, sending a signal instructing said each switch to connect its respective transducer to said second communication channel;

sending a pulse via said second communication channel, such that the pulse is received only by said first set of transducers; and storing the response received from said first set of transducers via said second communication channel.

19. A method according to claim 12, wherein:

said ultrasound apparatus further comprises a third plurality of switches, said first plurality of transducers are arranged in a two-dimensional array, thus creating rows and columns of transducers, each row of transducers is connected to said single communication channel via one of said first plurality of switches, and each column of transducers is connected to ground via one of said third plurality of switches, such that each of said first plurality of transducers can be uniquely addressed by one of said first plurality of switches and one of said third plurality of switches;

and wherein said step of generating each said first plurality of responses further comprises the step of:

identifying a third set of switches from said third plurality of switches comprising the switches connected to each of said first set of transducers, such that each of said first set of transducers is addressed by both one of said first plurality of switches and one of said third plurality of switches, and for each switch of said third set of switches, sending a signal instructing said each switch to connect its respective transducer to ground.

20. A computer-readable medium comprising instructions which, when executed by a computer, cause the computer to carry out the steps of the method of claim 12.

* * * * *